(12) United States Patent
Wardle et al.

(10) Patent No.: US 7,890,186 B2
(45) Date of Patent: Feb. 15, 2011

(54) RETRIEVAL DEVICES FOR ANCHORED CARDIOVASCULAR SENSORS

(75) Inventors: John L. Wardle, San Clemente, CA (US); Neal L. Eigler, Pacific Palisades, CA (US)

(73) Assignee: Pacesetter, Inc., Sylmar, CA (US)

( * ) Notice: Subject to any disclaimer, the term of this patent is extended or adjusted under 35 U.S.C. 154(b) by 1081 days.

(21) Appl. No.: 11/633,819

(22) Filed: Dec. 5, 2006

(65) Prior Publication Data
US 2007/0106328 A1    May 10, 2007

Related U.S. Application Data

(63) Continuation of application No. 10/672,443, filed on Sep. 26, 2003, now Pat. No. 7,149,587.

(60) Provisional application No. 60/413,758, filed on Sep. 26, 2002.

(51) Int. Cl.
*A61N 1/05* (2006.01)
(52) U.S. Cl. ........................ 607/119; 607/116
(58) Field of Classification Search ................. 607/116, 607/119
See application file for complete search history.

(56) References Cited

U.S. PATENT DOCUMENTS

| | | |
|---|---|---|
| 3,397,699 A | 8/1968 | Kohl et al. |
| 3,665,756 A | 5/1972 | Russell |
| 3,672,352 A | 6/1972 | Summers |
| 3,724,274 A | 4/1973 | Millar |
| 3,748,623 A | 7/1973 | Millar |
| 4,144,890 A | 3/1979 | Hess |
| 4,347,745 A | 9/1982 | Singh |
| 4,395,915 A | 8/1983 | Singh |
| 4,462,018 A | 7/1984 | Yang et al. |
| 4,632,125 A | 12/1986 | Webler et al. |

(Continued)

FOREIGN PATENT DOCUMENTS

EP    0 472 411 A1    2/1992

(Continued)

OTHER PUBLICATIONS

Steinhaus, David M., et al., "*Initial Experience with an Implantable Hemodynamic Montor*," Circulation, vol. 93, No. 4, pp. 745-752, Feb. 15, 1996.

(Continued)

*Primary Examiner*—Scott M Getzow
*Assistant Examiner*—Joseph M Dietrich
(74) *Attorney, Agent, or Firm*—Knobbe, Martens, Olson & Bear, LLP

(57) ABSTRACT

An anchoring device and a delivery method thereof can effectively provide a means for securing an implant to a wall of an internal organ within a patient in a variety of clinical applications. In one embodiment, an anchoring device used to retain a cardiac pressure measurement device is provided. The device is implanted in the body by deforming it to a small cross section profile, sliding it through a low profile delivery device and ejecting from the delivery device at a targeted site. The anchoring mechanism, when ejected from the delivery device, reverts back to pre-formed configuration and engages opposite sides of an organ wall, thereby anchoring the implant in the organ wall.

8 Claims, 13 Drawing Sheets

U.S. PATENT DOCUMENTS

| | | | |
|---|---|---|---|
| 4,679,144 A | 7/1987 | Cox et al. | |
| 4,726,232 A | 2/1988 | Koneval | |
| 4,745,928 A | 5/1988 | Webler et al. | |
| 4,785,822 A | 11/1988 | Wallace | |
| 4,852,581 A | 8/1989 | Frank | |
| 4,873,986 A | 10/1989 | Wallace | |
| 4,886,065 A * | 12/1989 | Collins, Jr. | 600/377 |
| 4,899,751 A | 2/1990 | Cohen | |
| 4,899,752 A | 2/1990 | Cohen | |
| 4,899,758 A | 2/1990 | Finkelstein et al. | |
| 4,967,749 A | 11/1990 | Cohen | |
| 4,972,847 A | 11/1990 | Dutcher et al. | |
| 4,974,596 A | 12/1990 | Frank | |
| 4,993,428 A | 2/1991 | Arms | |
| 5,083,573 A | 1/1992 | Arms | |
| 5,103,828 A | 4/1992 | Sramek | |
| 5,163,429 A | 11/1992 | Cohen | |
| 5,190,528 A | 3/1993 | Fonger et al. | |
| 5,314,418 A | 5/1994 | Takano et al. | |
| 5,324,325 A | 6/1994 | Moaddeb | |
| 5,324,327 A | 6/1994 | Cohen | |
| 5,344,439 A | 9/1994 | Otten | |
| 5,368,040 A | 11/1994 | Carney | |
| 5,398,692 A | 3/1995 | Hickey | |
| 5,464,434 A | 11/1995 | Alt | |
| 5,498,524 A | 3/1996 | Hall | |
| 5,522,266 A | 6/1996 | Nicholson et al. | |
| 5,522,819 A * | 6/1996 | Graves et al. | 606/113 |
| 5,535,752 A | 7/1996 | Halperin et al. | |
| 5,551,301 A | 9/1996 | Cowan | |
| 5,715,827 A | 2/1998 | Corl et al. | |
| 5,743,267 A | 4/1998 | Nikolic et al. | |
| 5,749,909 A | 5/1998 | Schroeppel et al. | |
| 5,752,976 A | 5/1998 | Duffin et al. | |
| 5,755,767 A | 5/1998 | Doan | |
| 5,758,652 A | 6/1998 | Nikolic | |
| 5,776,178 A | 7/1998 | Pohndorf et al. | |
| 5,861,003 A | 1/1999 | Latson et al. | |
| 5,861,018 A | 1/1999 | Fierbach | |
| 5,895,360 A | 4/1999 | Christopherson et al. | |
| 5,904,708 A | 5/1999 | Goedeke | |
| 5,919,210 A | 7/1999 | Lurie et al. | |
| 5,921,935 A | 7/1999 | Hickey | |
| 5,944,680 A | 8/1999 | Christopherson et al. | |
| 5,976,174 A | 11/1999 | Ruiz | |
| 5,993,395 A | 11/1999 | Shulze | |
| 6,021,352 A | 2/2000 | Christopherson et al. | |
| 6,024,704 A | 2/2000 | Meador et al. | |
| 6,024,756 A | 2/2000 | Huebsch et al. | |
| 6,099,479 A | 8/2000 | Christopherson et al. | |
| 6,106,476 A | 8/2000 | Corl et al. | |
| 6,117,086 A | 9/2000 | Shulze | |
| 6,120,457 A | 9/2000 | Coombes et al. | |
| 6,132,384 A | 10/2000 | Christopherson et al. | |
| 6,142,959 A | 11/2000 | Sarvazyan et al. | |
| 6,171,253 B1 | 1/2001 | Bullister et al. | |
| 6,178,349 B1 | 1/2001 | Kieval | |
| 6,193,670 B1 | 2/2001 | Van Tassel et al. | |
| 6,210,346 B1 | 4/2001 | Hall et al. | |
| 6,223,081 B1 | 4/2001 | Kerver | |
| 6,223,087 B1 | 4/2001 | Williams | |
| 6,234,973 B1 | 5/2001 | Meador et al. | |
| 6,240,321 B1 | 5/2001 | Janke et al. | |
| 6,264,611 B1 | 7/2001 | Ishikawa et al. | |
| 6,296,615 B1 | 10/2001 | Brockway et al. | |
| 6,309,350 B1 | 10/2001 | VanTassel et al. | |
| 6,328,699 B1 | 12/2001 | Eigler et al. | |
| 6,398,738 B1 | 6/2002 | Millar | |
| 6,409,674 B1 | 6/2002 | Brockway et al. | |
| 6,447,448 B1 | 9/2002 | Ishikawa et al. | |
| 6,553,263 B1 | 4/2003 | Meadows et al. | |
| 6,572,543 B1 | 6/2003 | Christopherson et al. | |
| 6,623,521 B2 | 9/2003 | Steinke et al. | |
| 6,629,951 B2 | 10/2003 | Laufer et al. | |
| 6,636,769 B2 | 10/2003 | Govari et al. | |
| 6,638,231 B2 | 10/2003 | Govari et al. | |
| 6,652,464 B2 | 11/2003 | Schwartz et al. | |
| 6,659,959 B2 | 12/2003 | Brockway et al. | |
| 6,746,404 B2 | 6/2004 | Schwartz | |
| 6,760,628 B2 | 7/2004 | Weiner et al. | |
| 6,767,327 B1 | 7/2004 | Corl et al. | |
| 6,783,499 B2 | 8/2004 | Schwartz | |
| 6,890,546 B2 | 5/2005 | Mollison et al. | |
| 6,939,376 B2 | 9/2005 | Shulze et al. | |
| 6,976,965 B2 | 12/2005 | Corl et al. | |
| 7,149,587 B2 | 12/2006 | Wardle et al. | |
| 7,229,415 B2 | 6/2007 | Schwartz | |
| 7,425,200 B2 | 9/2008 | Brockway et al. | |
| 7,481,774 B2 | 1/2009 | Brockway et al. | |
| 7,509,169 B2 | 3/2009 | Eigler et al. | |
| 2002/0077555 A1 | 6/2002 | Schwartz | |
| 2003/0055344 A1 | 3/2003 | Eigler et al. | |
| 2004/0148003 A1 | 7/2004 | Udipi et al. | |
| 2005/0288596 A1 | 12/2005 | Eigler et al. | |
| 2005/0288604 A1 | 12/2005 | Eigler et al. | |

FOREIGN PATENT DOCUMENTS

| | | |
|---|---|---|
| EP | 1 050 265 A2 | 11/2000 |
| EP | 1 057 448 A1 | 12/2000 |
| WO | WO 96/11722 | 4/1996 |
| WO | WO 99/56812 | 11/1999 |

OTHER PUBLICATIONS

Soufer, Robert, *"Treating a Sick Heart,"* Heart Disease, Nova Online web page, ©1997, WGBH.

Neergaard, Lauren, *"Daily Monitoring, Thanks to the Internet,"* CHealth web page, Feb. 22, 2000, ©2000, Healthbeat.

* cited by examiner

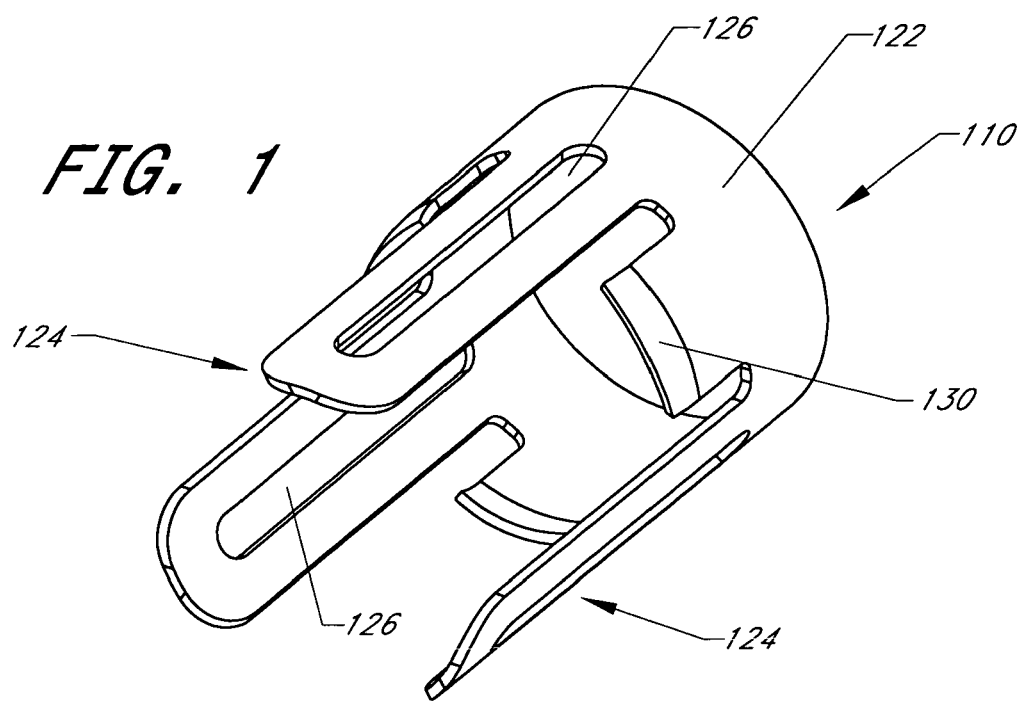
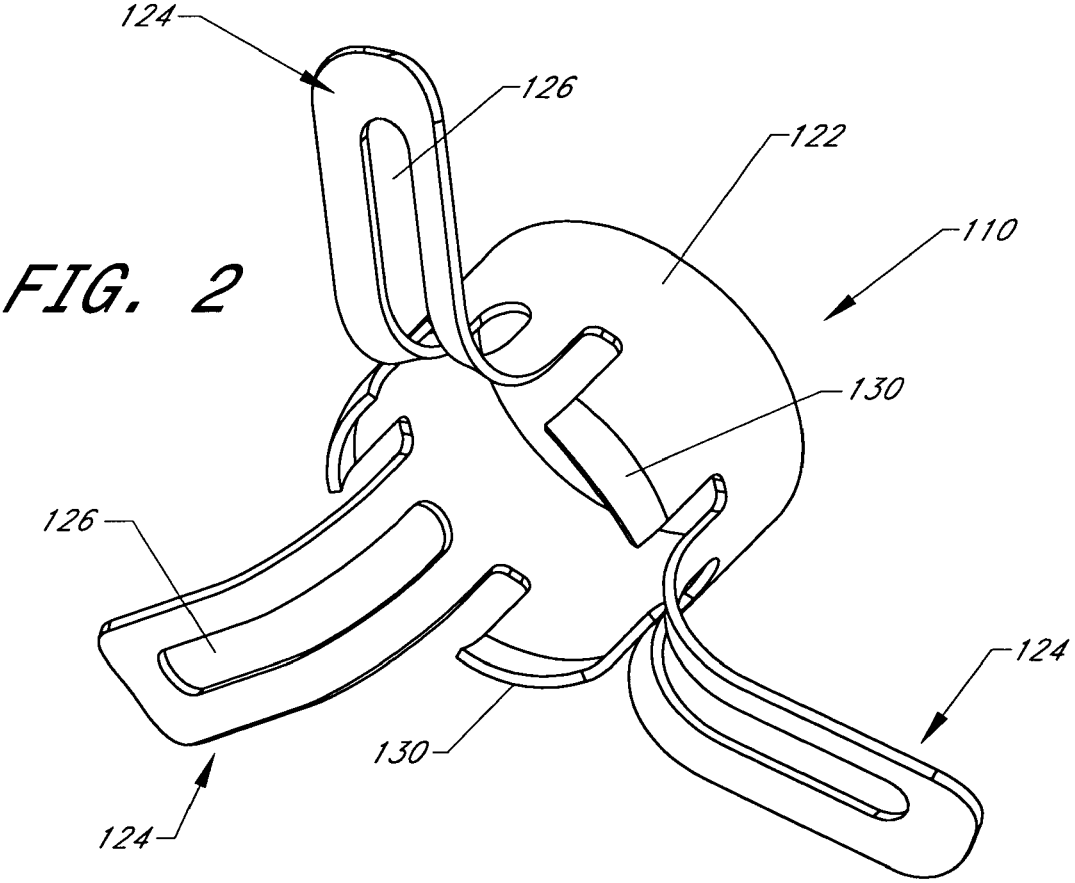

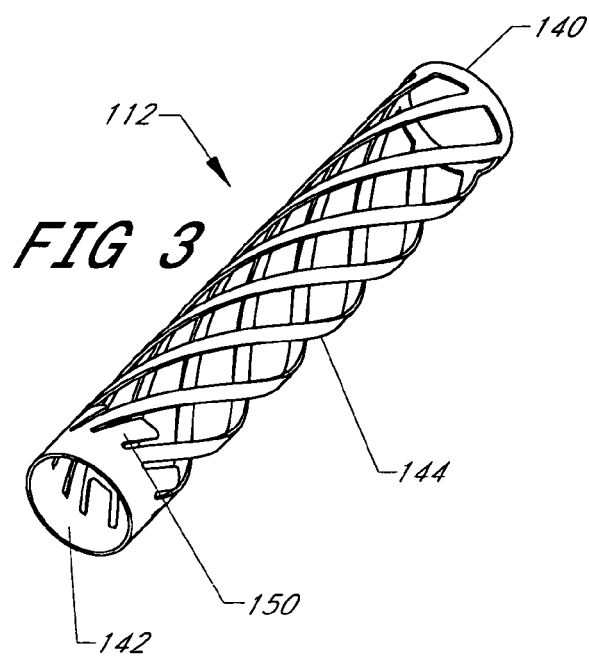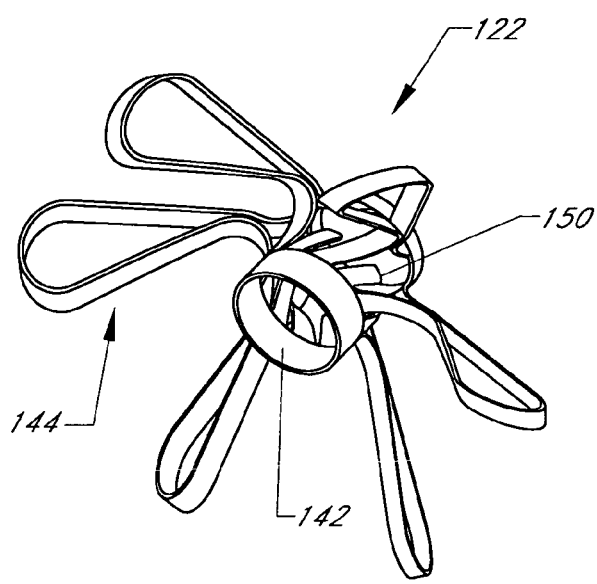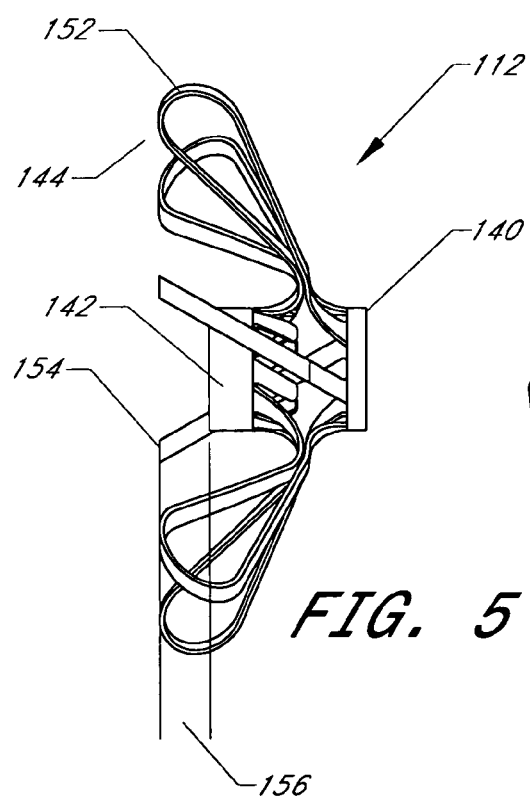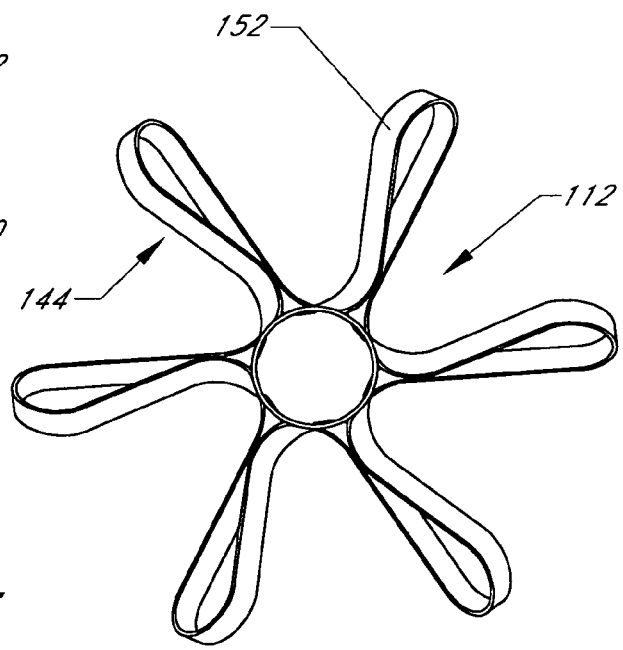

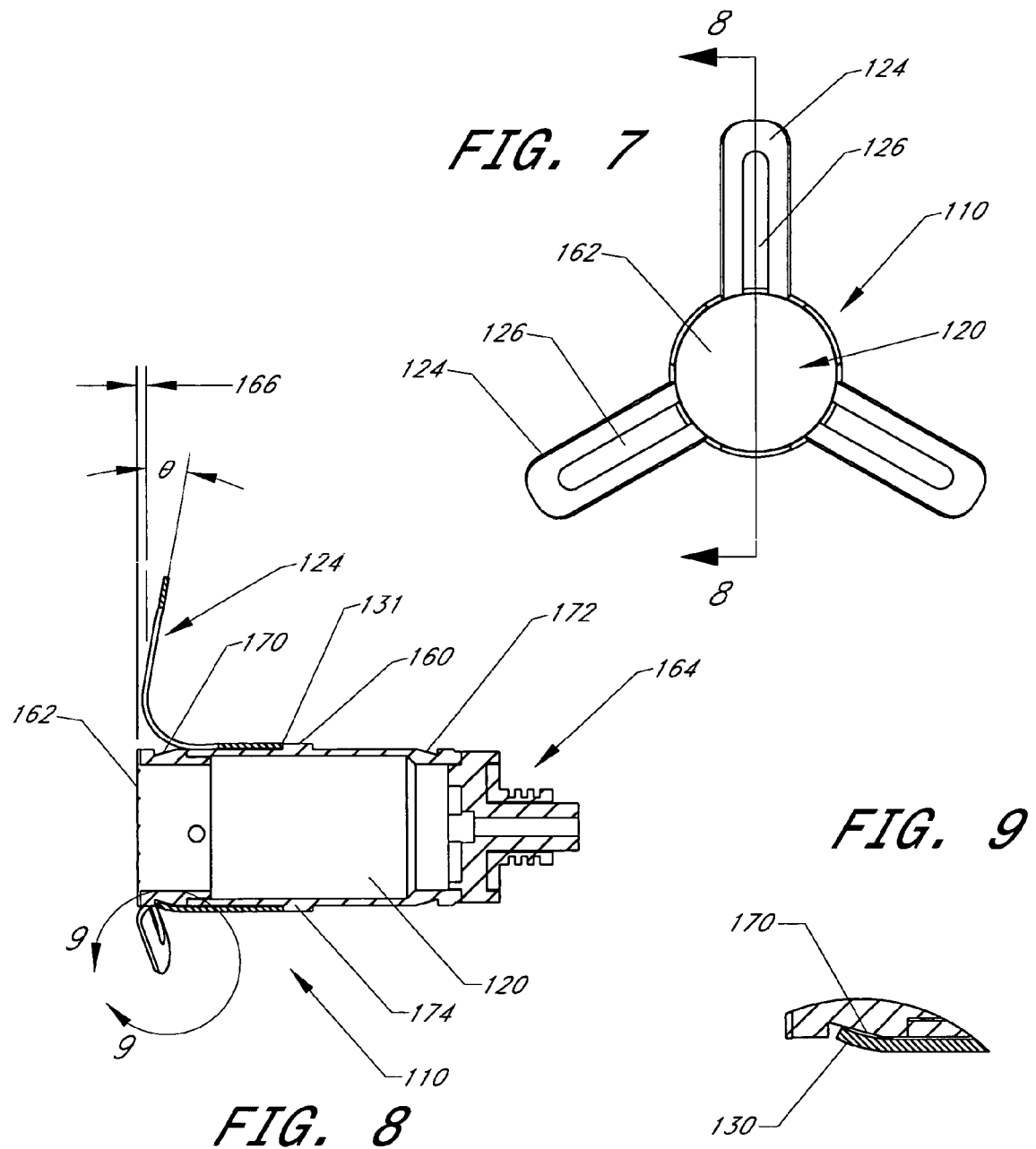

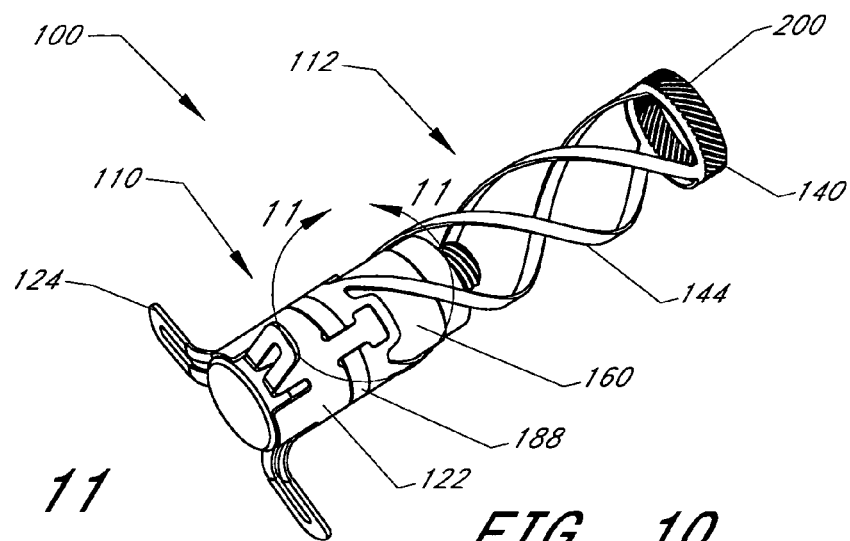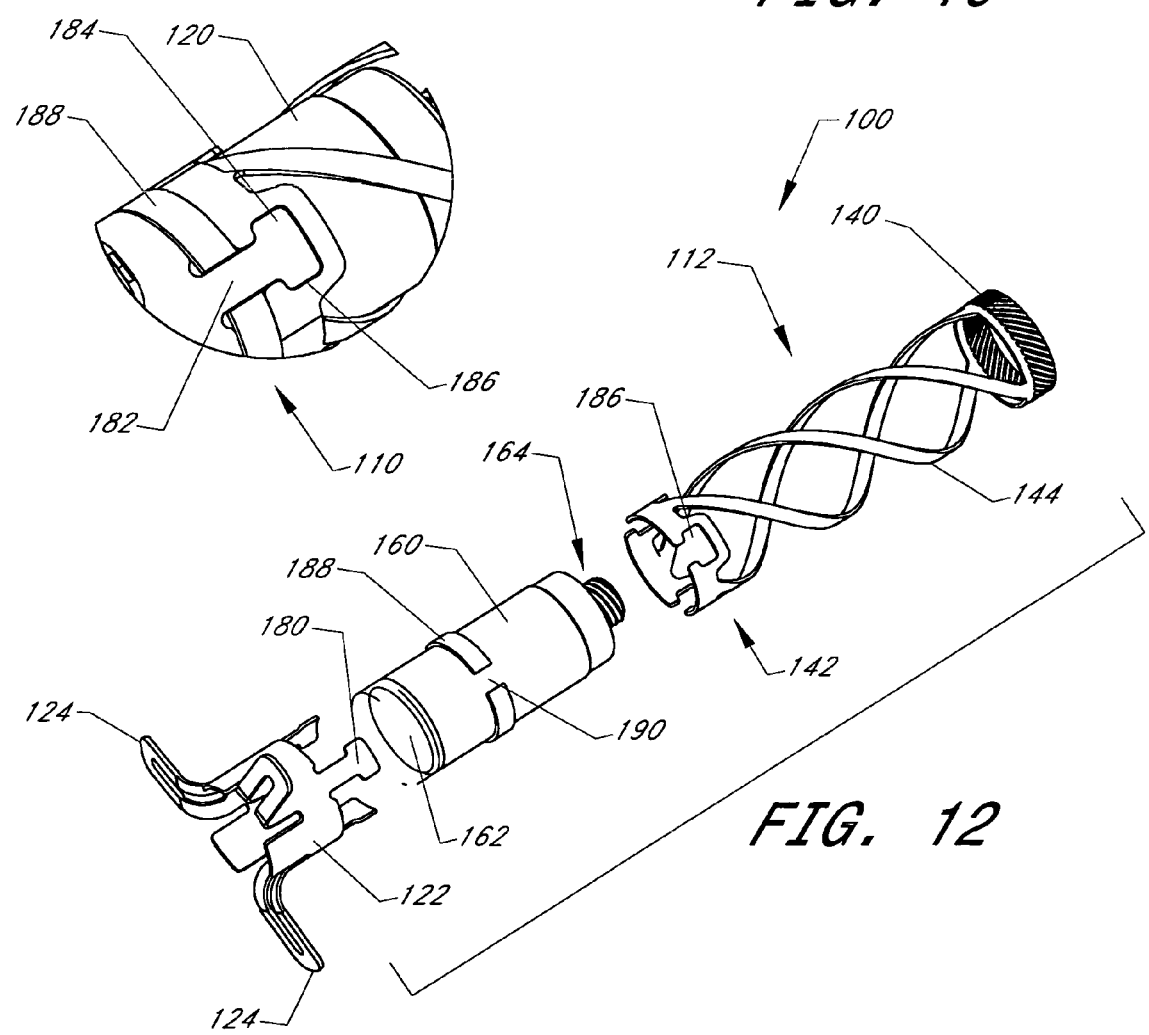

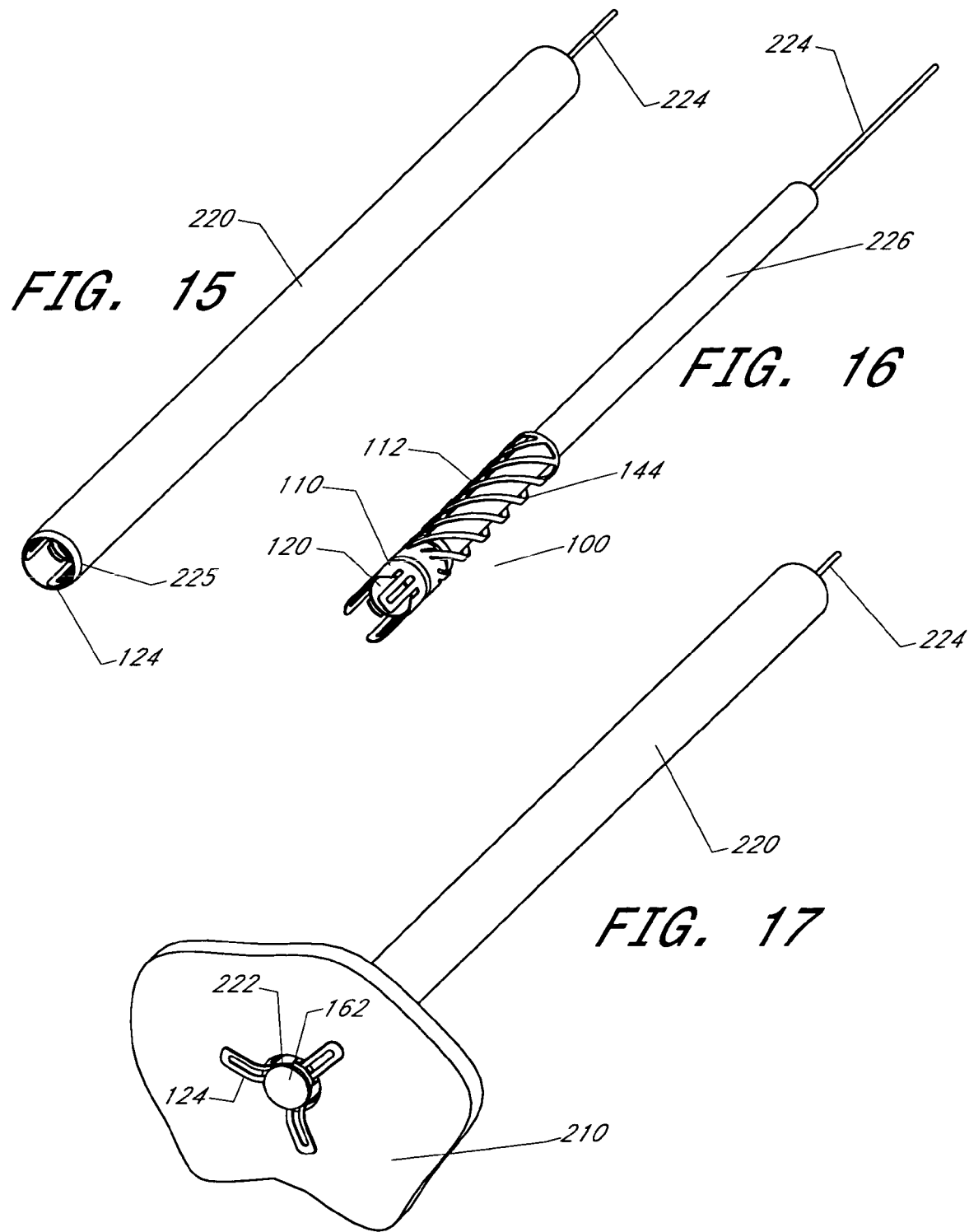

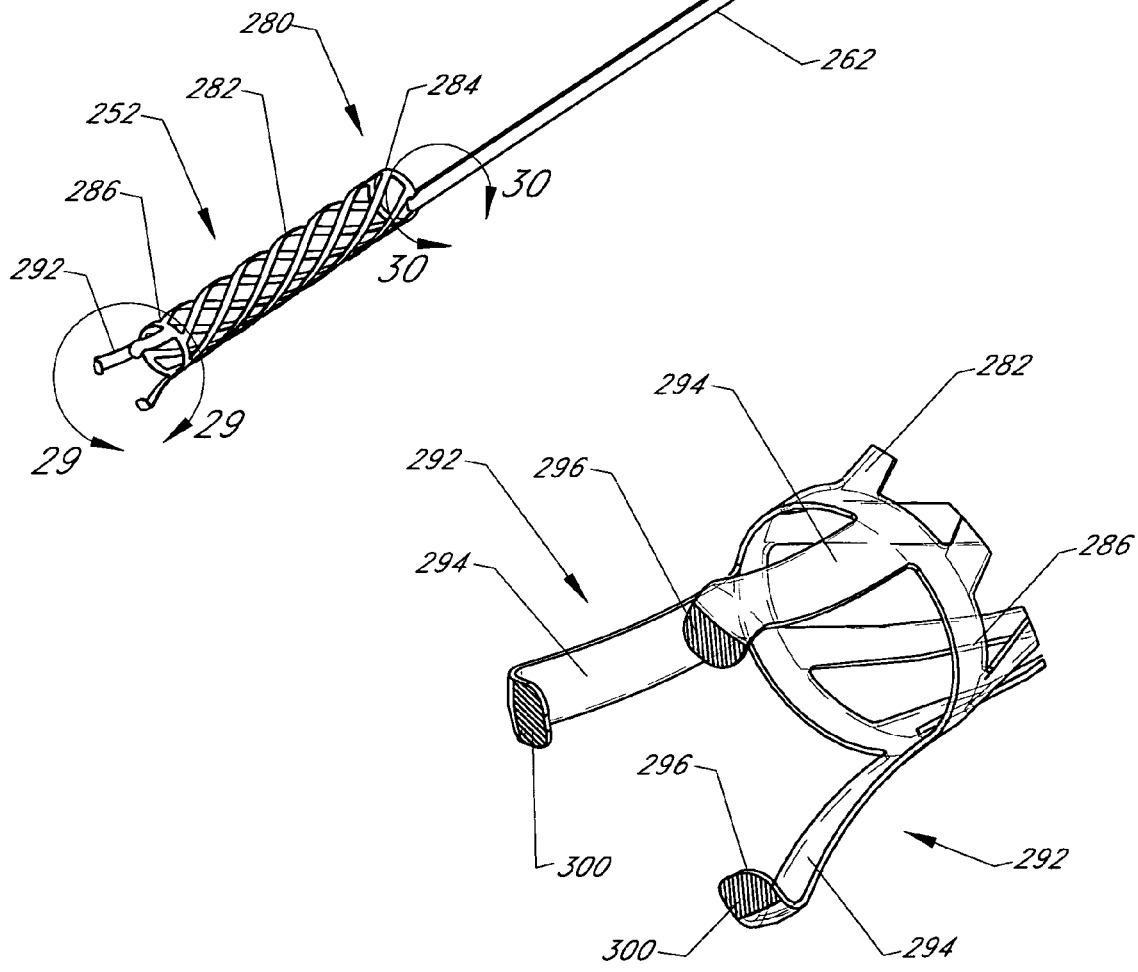

RETRIEVAL DEVICES FOR ANCHORED CARDIOVASCULAR SENSORS

CROSS REFERENCE TO RELATED APPLICATIONS

This application is a continuation of U.S. application Ser. No. 10/672,443 filed on Sep. 26, 2003, now U.S. Pat. No. 7,149,587, which claims priority under 35 U.S.C. §119(e) to U.S. Provisional Patent Application Ser. No. 60/413,758, filed on Sep. 26, 2002, all of which are incorporated herein by reference in their entirety.

BACKGROUND

1. Field of the Invention

This invention relates generally to cardiovascular anchoring devices and methods of deploying the same.

2. Description of the Related Art

Heart failure is a cardiovascular condition in which the heart fails to sufficiently supply the body with the oxygen rich blood the body requires, either at exercise or at rest. Congestive heart failure (CHF) is heart failure accompanied by a build-up of fluid pressure in the pulmonary blood vessels that drain the lungs. Transudation of fluid from the pulmonary veins into the pulmonary interstitial spaces, and eventually into the alveolar air spaces, is called pulmonary edema, and can cause shortness of breath, hypoxemia, acidosis, respiratory arrest, and death.

It is estimated that about four million people in the United States suffer from various degrees of heart failure. Although CHF is a chronic condition, the disease often requires acute hospital care. Patients are commonly admitted for acute pulmonary congestion accompanied by serious or severe shortness of breath. Acute care for CHF accounts for the use of more hospital days than any other cardiac diagnosis, and consumes in excess of seven and one-half billion dollars in the United States annually.

It is far more cost effective, and much better for the patient's health, if chronic CHF can be managed and controlled by the routine administration of appropriate drug therapy rather than by hospital treatment upon the manifestation of acute symptoms. Patients with chronic CHF are typically placed on triple or quadruple drug therapy to manage the disease. The drug regimen commonly includes diuretics, vasodilators such as ACE inhibitors or A2 receptor inhibitors, and inotropic agents usually in the form of cardiac glycosides such as Digoxin. Patients may also be placed on beta blockers such as Carvedilol.

As with all drugs, these agents must be taken in doses sufficient to ensure their effectiveness. Problematically, however, over-treatment can lead to hypotension, renal impairment, hyponatremia, hypokalemia, worsening CHF, impaired mental functioning, and other adverse conditions. Adding to the challenge of maintaining proper drug dosage is the fact that the optimal dosage will depend on diet, particularly salt and fluid intake, level of exertion, and other variable factors. Adding further to the problem of managing this condition is the fact that patients frequently miss scheduled doses by forgetting to take pills on time, running out of medications, or deciding to stop medications without consulting their physician. It is important, therefore, that the patient's condition be monitored regularly and thoroughly, so that optimal or near optimal drug therapy can be maintained. This monitoring is itself problematic, however, in that it requires frequent visits with a caregiver, resulting in considerable inconvenience and expense.

SUMMARY OF THE INVENTION

In view of the above discussion, it is desirable to provide a system by which a patient's congestive heart failure can be monitored routinely or continuously with minimal attendance by a caregiver, and then only when actually required. It is also desirable that such a system include a means for communicating diagnostic information not only to the physician but to the patient as well, so that the patient can continue or modify his own drug therapy appropriately and generally without the direct intervention of a physician. One example of such a system is described in U.S. Pat. No. 6,328,699 to Eigler et al., herein incorporated by reference (referred to herein as "the Eigler patent"). The systems and methods described in several embodiments of the Eigler patent generally involve implantation of a pressure sensor within a portion of the patient's heart (such as the left atrium) in order to continuously monitor a fluid pressure in the portion of the heart.

Notwithstanding the particular advantages of the systems and methods described in the Eigler patent, there remains room for improvement to the systems and methods used for anchoring a sensor to a wall of the patient's heart (such as the atrial septum).

Preferred embodiments of the present invention provide an anchoring device and a method of delivery which can effectively be used to deploy an anchoring mechanism for a variety of clinical applications. In one embodiment, an anchoring device is configured to cross the septum between the right and left atrium and trap itself between the two chambers such that a pressure sensing member is exposed to the left atrium. The device is configured in a manner that will allow it to position the pressure sensing member at a desired location relative to the septal wall while conforming to anatomical variations.

According to one embodiment, radiopaque markers can be provided on the anchor and/or the delivery and retrieval apparatus. One advantage of such markers is to enable fluoroscopic guidance of the devices during delivery and retrieval procedures.

According to one embodiment, an implantable device is provided. The device of this embodiment comprises a proximal anchor having one or more helical legs extending between a proximal ring and a distal ring. The device also comprises a distal anchor having one or more legs. The proximal and distal anchors of this embodiment are preferably configured to be movable between a collapsed delivery position and an expanded position in which the proximal and distal anchors secure the implant to a wall of an organ within a patient. The device further includes a diagnostic and/or therapeutic implant configured to be supported by the proximal and distal anchors. In one embodiment, the diagnostic tool includes apparatus operable to measure one or more physiological parameters. In one embodiment, the diagnostic tool includes apparatus operable to measure pressure, oxygen levels, or electrical activity, or some combination thereof. In one embodiment, the therapeutic tool comprises apparatus operable to deliver one or more pharmaceutical agents to the patient. In another embodiment, the therapeutic tool includes apparatus operable to deliver one or more electrical signals or pulses to the patient. In one embodiment, the implant comprises a pressure sensor (or pressure transducer). In other embodiments, the implant includes, but is not limited to, sensors, sensing and stimulating electrodes, ultrasound transducers, drug delivery systems, pacing leads, electrocardiogram leads, oxygen partial pressure sensors, oxygen saturation sensors, and any other device that one desires to securely anchor to a wall of an internal organ.

Another embodiment provides a system for diagnosing and/or treating a condition in a patient. The system of this embodiment comprises an implant configured to be implanted within a patient, a proximal anchor comprising at least one helical leg configured to expand from a compressed state to a relaxed state, and a distal anchor comprising at least one leg configured to expand from a compressed state to an expanded state. The proximal anchor and the distal anchor of this embodiment are preferably configured to sandwich an atrial septum wall (or the left atrial free wall, the pulmonary vein wall, or any other suitable wall of a heart) between the proximal anchor leg and the distal anchor leg and to support the implant in the septum wall. The system of this embodiment also preferably comprises a delivery catheter configured to deploy the sensor, the proximal anchor, and the distal anchor in the septum wall. In one embodiment, the system is particularly suited to monitoring congestive heart failure in the patient.

Another embodiment provides a system for monitoring a patient for congestive heart failure comprising an implantable pressure sensor and a means for contacting a proximal wall and a distal wall of an organ to anchor said pressure sensor to the organ wall. The system can further comprise a means for delivering said implantable sensor and said means for contacting to said organ wall. In another embodiment, the system further comprises a means for retrieving said implantable pressure sensor from the organ wall.

In another embodiment, a method of monitoring congestive heart failure in a patient is provided. The method of this embodiment comprises providing a pressure sensor secured to a proximal anchor and a distal anchor, and delivering the pressure sensor to a hole in an atrial septum of the patient's heart. The method further comprises deploying the pressure sensor with the proximal anchor on a proximal side of the septum, and the distal anchor on a distal side of the septum; monitoring a fluid pressure in the left atrium of the patient's heart.

Another embodiment provides a method of monitoring congestive heart failure within a patient. The method of this embodiment comprises providing an implantable pressure sensor and coupling said implantable pressure sensor to a means for anchoring said pressure sensor in an organ wall. The method further comprises delivering said pressure sensor and said means for anchoring to said organ wall, and causing said means for anchoring said pressure sensor in said organ wall to expand, thereby capturing said organ wall and anchoring said pressure sensor thereto. In another embodiment, the method can further comprise removing said pressure sensor and said means for anchoring from said organ wall. In one embodiment, said removing is performed by introducing a means for retrieving said means for anchoring.

According to still another embodiment, a method of anchoring a device in the heart of a patient is provided. The method includes providing an implantable cardiac anchoring device comprising a proximal anchor having at least one helical leg and a distal anchor having at least one linear leg. The method comprises attaching an implantable tool, (referred to herein as an "implant"), to the implantable cardiac anchoring device, positioning a tubular delivery catheter in a wall of a patient's heart, and inserting the implant and the implantable cardiac anchoring device into the tubular delivery catheter. The method further includes deploying the sensor and the implantable cardiac anchoring device such that the sensor is retained in a transverse orientation relative to the wall.

According to further embodiments, methods and apparatus are also provided for engaging and removing the anchoring mechanism from its deployed position. According to one embodiment, a retrieval device is configured to retrieve a cardiac anchoring device from a position deployed in a wall of an organ within a patient. The retrieval device of this embodiment comprises a retrieval head having a plurality of grasping hooks extending from a distal end thereof, a ribbon of sufficient length to extend from a retrieval location within a patient to a location outside of a patient. The grasping hooks of this embodiment are preferably configured to engage a proximal ring of a proximal anchor.

According to another embodiment, a method is provided for retrieving a cardiac anchoring device from a heart of a patient using a retrieval device. The method of this embodiment comprises placing a retrieval device in a delivery catheter. The retrieval device placed in the catheter comprises a retrieval head with a plurality of distally-extending grasping hooks and a control ribbon attached to the retrieval device. The method further comprises guiding said delivery catheter into a position adjacent a sensor device anchored to a wall of the patient's heart. The retrieval device is then engaged on a proximal ring of a proximal anchor secured to the sensor device, and the proximal ring of the proximal anchor is pulled into the delivery catheter. The method is continued by holding the sensor device stationary while pulling the retrieval device, the proximal ring of the proximal anchor and the delivery catheter proximally, thereby returning an anchor leg of said proximal anchor to a compressed position. The delivery catheter is advanced distally while holding the proximal anchor and the sensor device stationary in order to compress at least one expanded leg of the distal anchor attached to the sensor device. Once the anchors are compressed, the sensor device, the proximal anchor and the distal anchor are all pulled completely into the lumen of the delivery catheter, the delivery catheter is removed from the patient.

BRIEF DESCRIPTION OF THE DRAWINGS

FIG. 1 is a perspective view of one embodiment of a distal anchor in a compressed state for deployment in a patient.

FIG. 2 is a perspective view of the distal anchor of FIG. 1 in an expanded state.

FIG. 3 is a perspective view of one embodiment of a proximal anchor in a compressed state.

FIG. 4 is a perspective view of the proximal anchor of FIG. 3 in an expanded state.

FIG. 5 is a side view of the proximal anchor of FIG. 4.

FIG. 6 is a front view, looking proximally at the proximal anchor of FIG. 5.

FIG. 7 is a front view, looking proximally at a distal anchor and a sensor mounted to the distal anchor.

FIG. 8 is a cross-sectional view of the distal anchor and sensor of FIG. 7 taken through line 8-8.

FIG. 9 is a detail view of a portion of the distal anchor and sensor of FIG. 8, taken at line 9-9.

FIG. 10 is a perspective view of one embodiment of an assembly of a proximal anchor, a distal anchor, and a sensor.

FIG. 11 is a detail view of a portion of the assembly of FIG. 10, taken through line 11-11.

FIG. 12 is an exploded view of the proximal anchor, distal anchor and sensor of FIG. 10.

FIG. 15 is a perspective view of a delivery catheter with a portion of a distal anchor visible at the distal end of the delivery catheter.

FIG. 16 is a perspective view of the assembly of FIG. 15 shown with the delivery catheter removed to show detail.

FIG. 17 is a perspective view of a distal anchor and a sensor deployed on a distal side of an atrial septum wall.

FIG. 28 is a perspective view of an alternative embodiment of a retrieval device.

FIG. 29 is a detail view of a distal portion of the retrieval device of FIG. 28, taken through line 29-29.

FIG. 30 is a detail view of a proximal portion of the retrieval device of FIG. 28, taken through line 30-30.

DETAILED DESCRIPTION OF THE PREFERRED EMBODIMENTS

Figure 13:
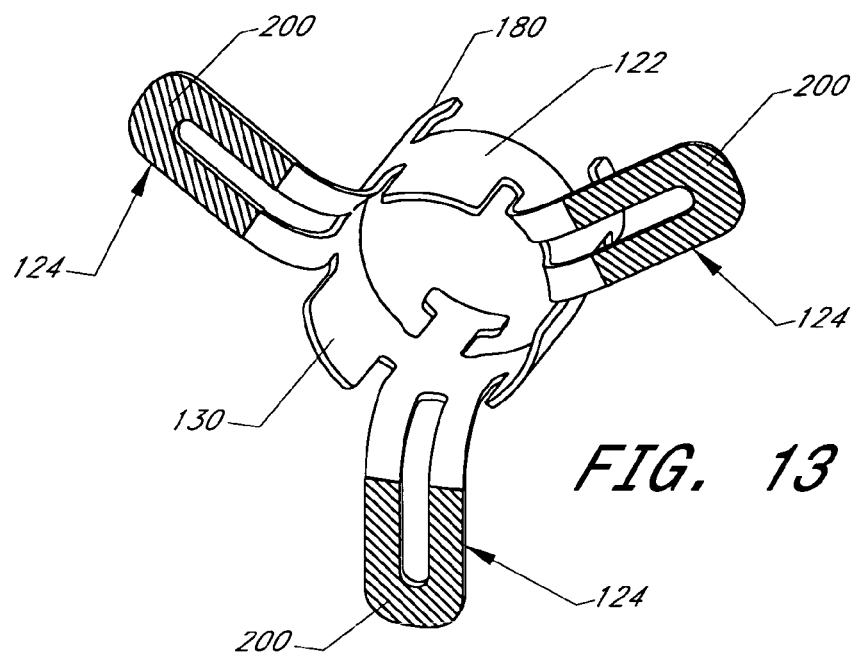
FIG. 13 is a perspective view of an alternative embodiment of a distal anchor in an expanded state.

The following embodiments are described in relation to the placement of an anchoring and pressure measurement device within an atrial septum wall. The skilled artisan will recognize that certain aspects of the present invention can be applied to other applications as well. For example, the anchor devices described herein can be configured to anchor any suitable diagnostic and/or therapeutic implant to a wall of an organ within a patient. Therefore, it is intended that the scope of the present invention not be limited by the particular embodiments described below, but should be determined only by a fair reading of the claims.

Throughout the following description, the terms "proximal" and "distal" are used to describe relative positions, locations and/or orientations of various components. As used herein, the term "distal" is used in its ordinary sense, and generally refers to objects and locations that are further along a trans-vascular path. Similarly, the term "proximal" is used in its ordinary sense, and refers without limitation, to objects and locations that are closer along a trans-vascular path to an operator of a trans-vascular device. For example, in some embodiments the most proximal end of a catheter is the end that is operated by a clinician performing a procedure within a patient with the catheter. Similarly, in such embodiments the distal-most end of a catheter is the end placed furthest into the body of the patient and furthest from the clinician performing the procedure. The terms "proximal" and "distal" are used herein with reference to certain preferred embodiments of the orientation of certain components during a procedure. The skilled artisan will recognize however, that in alternative embodiments the directions of "proximal" and "distal" as used herein may be reversed with respect to a single component used in a similar procedure.

Turning now to the figures, embodiments of cardiovascular anchoring devices for use in anchoring an implantable diagnostic or therapeutic implant to an organ wall (such as an atrial septum wall) will now be described. In one embodiment, the diagnostic tool comprises apparatus operable to measure one or more physiological parameters. In one embodiment, the diagnostic tool comprises apparatus operable to measure pressure, oxygen levels, and/or electrical activity. In one embodiment, the therapeutic tool comprises apparatus operable to deliver one or more pharmaceutical agents to the patient. In another embodiment, the therapeutic tool includes apparatus operable to deliver one or more electrical signals or pulses to the patient. Implants also include, but are not limited to, sensors, sensing and stimulating electrodes, ultrasound transducers, drug delivery systems, pacing leads, electrocardiogram leads, oxygen partial pressure sensors, oxygen saturation sensors, and any other device that one desires to securely anchor to a wall of an internal organ. In some embodiments, the implant comprises a sensor, and in one particular embodiment, the implant is a pressure sensor or transducer. The figures included herein illustrate a straight device and deployment apparatus for the purpose of demonstration. However, one skilled in the art will understand that, in use, the delivery catheter and contained components will typically be substantially flexible or may assume other non-straight shapes. For example, a delivery catheter can be configured to include a pre-shaped curve or a pre-shaped stylet in order to facilitate navigation of a patient's tortuous vasculature. As will also be clear to the skilled artisan, the flexibility of certain components will be particularly advantageous for navigation through tortuous anatomy.

FIGS. 1-14 illustrate embodiments of an anchor and sensor assembly 100 comprising a distal anchor 110 and a proximal anchor 112 configured to secure a sensor 120 to a wall of an internal organ (such as a left atrium of a heart) within a patient. The proximal and distal anchor components 110 and 112 are configured to be compressed to a delivery state such that they can be placed within a tubular delivery catheter. The anchors 110 and 112 are further configured such that when they are released from their compressed state, they will relax to assume a preformed, expanded configuration in which they engage opposite sides of a septum wall 210 (e.g. see FIGS. 20 and 21) in order to support the sensor 120 in an operative position.

Many of the embodiments of implantable devices shown and described herein are preferably configured to be deployed via a tubular, flexible delivery catheter that can be guided either alone or over a guidewire to a delivery location within a patient. A delivery catheter for use in delivering and deploying an implantable device preferably comprises an internal diameter that is at least as large as the outer diameter of the distal and proximal anchors in their compressed states. In some embodiments, a delivery catheter can be configured to be sufficiently large in diameter to allow the catheter to be filled with a continuous column of fluid. This advantageously allows for simultaneous monitoring of a fluid pressure at the distal end of the catheter through the continuous fluid column surrounding the anchoring system in the catheter. Such an arrangement would also advantageously allow for the injection of a radiographic contrast medium through the delivery catheter in order to determine the precise location of the catheter tip in the cardiovascular system. The skilled artisan will recognize that other embodiments of delivery catheters incorporating additional fluid-carrying lumens can also be used to deliver an implantable anchoring device.

In order to allow the proximal and distal anchors 110 and 112 to self-expand from a compressed state to an expanded state, they are preferably made from materials that exhibit superelastic and/or shape memory characteristics. Alternatively, the anchors could be made from other non-superelastic or non-shape memory materials as desired. For example, suitable materials for fabrication of the proximal and distal anchors include, but are not limited to, nickel titanium alloys (NiTi or NITINOL), cobalt-chromium alloys, stainless steel, ELGILOY, MP35N or other biocompatible, superelastic, and/or shape memory materials that are well known to those skilled in the art of clinical medical devices. The anchors can be made by any suitable process appropriate for a particular material. For example, the anchors could be molded, machined, laser cut, etc as desired.

FIGS. 1 and 2 illustrate one embodiment of a distal anchor 110 in a compressed state and an expanded state respectively. The distal anchor 110 generally comprises a circular base portion 122 with a plurality of legs 124 extending distally therefrom. In the illustrated embodiment, the legs 124 include slots 126 to advantageously promote tissue overgrowth in a deployed position, which will advantageously aid in securement of the device to the septum wall. In alternative embodiments, the legs 124 can be solid. As shown, the distal anchor 112 also comprises struts or locking tabs 130 configured to engage a portion of the sensor 120 as will be further described below. In its compressed state, as shown in FIG. 1, the distal anchor 124 occupies a substantially cylindrical shape, thereby allowing it to be placed within a cylindrical, tubular delivery catheter or delivery sheath.

In an expanded shape, as shown in FIG. 2, the legs 124 of the distal anchor 110 bend outwards and proximally. In one embodiment, the legs 124 bend outwards until they are substantially perpendicular to the longitudinal axis of the cylindrical base portion 122. In alternative embodiments, the legs bend proximally until they are oriented at more than 90° to the longitudinal axis of the cylindrical base 122 as shown for example in FIG. 8. In such embodiments, the angle θ (which represents the amount beyond perpendicular to the longitudinal axis that the legs 124 can bend) can be between about 0° and about 20°. In some preferred embodiments, the angle θ can be between about 5° and about 15°, and in one specific preferred embodiment, the angle θ can be about 10°. In one preferred embodiment, the angle θ will preferably be reduced to zero degrees when the distal anchor 110 is deployed on a distal side of a septum wall 210 (see FIG. 20) with a proximal anchor 112 on the proximal side of the wall 210 due to the opposing force of the proximal anchor 112. Thus, in a preferred embodiment, the angle θ is selected along with a spring constant of the distal anchor legs 124 such that an opposing force applied by the proximal anchor 112 through a septum wall of a particular thickness (as will be further described below) will cause the angle θ to be substantially reduced to zero or to deflect a small amount in the distal direction so as to conform with a substantially concave left atrial surface.

FIGS. 3-6 illustrate one embodiment of a proximal anchor 112 in compressed (FIG. 3) and expanded (FIGS. 4-6) states. In its compressed state, the proximal anchor 112 occupies a substantially cylindrical space such that it can be placed in a cylindrically tubular delivery catheter. The proximal anchor 112 generally includes a proximal ring 140 and a distal ring 142 with a plurality of legs 144 extending therebetween. The proximal anchor 112 can include any number of anchor legs 144 as desired. For example, in the embodiment illustrated in FIG. 3, the proximal anchor comprises six anchor legs 144. Alternatively, the proximal anchor 112 can include a greater or lesser number of anchor legs 144. The proximal anchor 112 can also include struts or locking tabs 150 which can be used to secure the sensor 120 to the proximal anchor as will be further described below.

In the embodiment of FIG. 3, the anchor legs 144 are configured to follow a helical path between the proximal ring 140 and the distal ring 142. In one preferred embodiment, the helical path of the anchor legs 144 passes through 360 degrees between the proximal ring 140 and the distal ring 142. In alternative embodiments, the proximal anchor 112 can be longer and/or the legs 144 can pass through 720 degrees. In general, it is desirable that the legs pass through a substantially whole number of complete circles between the proximal and distal rings 140, 142. This configuration allows the proximal anchor 112 to negotiate the tortuous path that is typically encountered during delivery of the device to a desired location within a patient. The spiral or helical shape of the proximal anchor is particularly advantageous because this configuration equalizes bending stresses experienced by the anchor legs 144 in order to maintain an internal lumen (typically with a circular cross-section) of the proximal anchor 112 as the device is navigated through a tortuous path. Additionally, the illustrated configuration advantageously increases flexibility of the proximal anchor 112 and reduces its diameter to allow the anchor to be more effectively negotiated through a tortuous anatomy without damaging the device or injuring the patient.

FIGS. 4-6 illustrate the proximal anchor 112 in its expanded state. As shown, proximal anchor 112 preferably assumes a substantially "mushroomed" shape in its expanded state. In moving between the compressed and expanded states (assuming the distal ring 142 is held substantially stationary), the anchor legs 144 preferably unwind and buckle outwards and distally relative to the proximal ring 142. As shown, the proximal anchor 112 preferably "unwinds" such that the proximal ring 140 rotates relative to the distal ring 142 as the anchor 112 moves between its compressed and expanded states. The amount of rotation of the proximal ring relative to the distal ring will typically be a function of the final resting distance between the proximal ring and the distal ring.

In their fully expanded state, the anchor legs 144 preferably bend outwards and distally until each leg 144 forms a loop 152 with a distal most edge 154 that is positioned substantially distally from the distal edge of the distal ring 142. In some preferred embodiments, the anchor assembly can be configured such that, in free space (i.e. with no tissue or material between the proximal and distal anchors), the distal edge 154 of the proximal anchor leg loops 152 and the proximal tissue-contacting surface of the distal anchor 110 can actually overlap by up to about 0.06". In some preferred embodiments the overlap can be between about 0.03" and about 0.05", and in one specifically preferred embodiment, the distance is about 0.04". In some embodiments (as shown in FIG. 5), the distance 156 between the distal edge 154 of the proximal anchor leg loops 152 and the distal edge of the distal ring 142 of the proximal anchor can be between about 0.040" and about 0.070". In some preferred embodiments, the distance 156 is between about 0.050" and about 0.060", and in one particular preferred embodiment, the distance 156 is about 0.054". By providing the proximal and distal anchor legs 144 and 124 with sufficient resilience that they relax to overlapping positions, it can be assured that the assembly will be able to securely anchor to even the thinnest of septum walls.

FIGS. 7-9 illustrate the distal anchor 110 mounted to a sensor 120. In the illustrated embodiment, the sensor 120 is a pressure sensor having a substantially cylindrical body 160 with a pressure sensing face 162 at its distal end, and a lead-attachment interface 164 at its proximal end. In one preferred embodiment, as shown, the lead-attachment interface comprises a series of annular notches which can be engaged by a tightly-wound coil to secure the electrical lead. In some embodiments, a lead-attachment mechanism can be welded in place (such as by laser welding) on the sensor 120 in order to provide a more secure connection. In another embodiment, the lead-attachment interface 164 can comprise screw threads. Alternatively, the skilled artisan will recognize that any number of suitable alternative interfaces could also be used. Additional details of a suitable pressure sensor are provided, for example, in U.S. Pat. No. 6,328,699 to Eigler et al. ("the Eigler patent"), which is incorporated herein by reference and made part of the present disclosure. In alternative embodiments, the sensor 120 can be configured to serise and/or monitor any desired parameter within a patient.

In the embodiment of FIGS. 7-9, the distal anchor 110 is secured to the sensor 120 by struts or locking tabs 130 on the anchor, which engage an angled annular groove 170 which circumscribes a distal portion of the sensor 120. The locking tabs 130 extending distally from the distal anchor 110 (as shown in FIGS. 1 and 2) are preferably bent slightly radially inwards such that they will engage the distal annular groove 170 in the sensor as shown in the detail view of FIG. 9. Similarly, a proximal annular groove 172 is provided to be engaged by the locking tabs 150 of the proximal anchor 112 (shown in FIG. 3). The anchor-to-sensor attachment system illustrated in FIGS. 7-9 allows the anchors 110 and 112 to rotate about the sensor 120. In some situations it is desirable to prevent rotation of the anchors relative to the sensor 120 by spot-welding the proximal and/or distal anchors to an annular flange 174 provided on the sensor 120. Alternatively, in place of an annular groove, the sensor could comprise angled notches for receiving the locking tabs in a single rotational orientation on the sensor 120. Alternatively still, other attachment systems can also be used, such as welds, adhesives, and other mechanical fasteners.

FIG. 8 illustrates a cross-sectional view of the sensor 120 attached to a distal anchor. In some embodiments, it may be desirable to vary the distance 166 between a distal most edge of a distal anchor leg 124 (in an expanded state as shown) and the pressure sensing face 162 of the sensor 120. In one preferred embodiment, the distance 166 is preferably zero, i.e. the pressure sensing face 162 is preferably substantially co-planar with the distal most point of a deployed distal anchor leg 124. Such a configuration will preferably advantageously place the pressure sensing face 162 substantially flush with the atrium wall, thereby reducing the hemodynamic effect experienced by the sensor 120. In alternative embodiments, it may be desirable that the sensor 120 be moved distally such that the pressure sensing face extends distally outwards from the distal anchor. Alternatively still, it may be desirable to support the sensor 120 within the distal anchor 110 such that the sensor face 162 is recessed within the distal anchor 110. The location of the sensor face relative to the distal anchor can be varied by changing a location of the distal annular groove 170 and/or by varying a size of the locking tabs 130.

FIGS. 10-14 illustrate an alternative embodiment of an anchor and sensor assembly 100 wherein the components are attached to one another with interlocking mechanical fasteners. As shown, the proximal anchor 112, the distal anchor 110, and the sensor 120 include interlocking structures configured to mechanically interconnect the assembly components in such a way as to limit both axial and rotational movement of the components relative to one another.

The distal anchor of FIGS. 10-12 comprises a plurality of fingers 180 which extend proximally from the cylindrical base portion 122. As shown, each finger 180 can include a narrow neck section 182 and a wider proximal tab section 184. The proximal anchors 112 can include correspondingly shaped slots 186 in the distal ring 142 to receive the fingers 180. The sensor 120 can also include corresponding interlocking structures configured to engage structures on the distal and/or proximal anchors 110, 112. As shown the sensor 120 can include raised sections 188 around the circumference of the cylindrical body 160. The raised sections 188 can be positioned so as to leave gaps 190 for receiving the neck sections 182 of the fingers 180. The raised sections 188 can be machined into the cylindrical body 160 of the sensor, or they can comprise independent segments welded, adhered, or otherwise secured to the cylindrical body 160 of the sensor 120. The components can be assembled as shown in FIG. 10 to provide a secure and substantially immobile connection between the proximal anchor 112, the sensor 120 and the distal anchor 110. The specific geometry of the interlocking structures of FIGS. 10-12 are intended to be merely exemplary, and the specific shapes of the fingers 180, slots 186, and spaces 190 can alternatively include a variety of different geometric shapes in order to provide a secure connection between the components. If desired, the interlocking structures can also be welded together once they are assembled, thereby further securing the connection.

Figure 14:
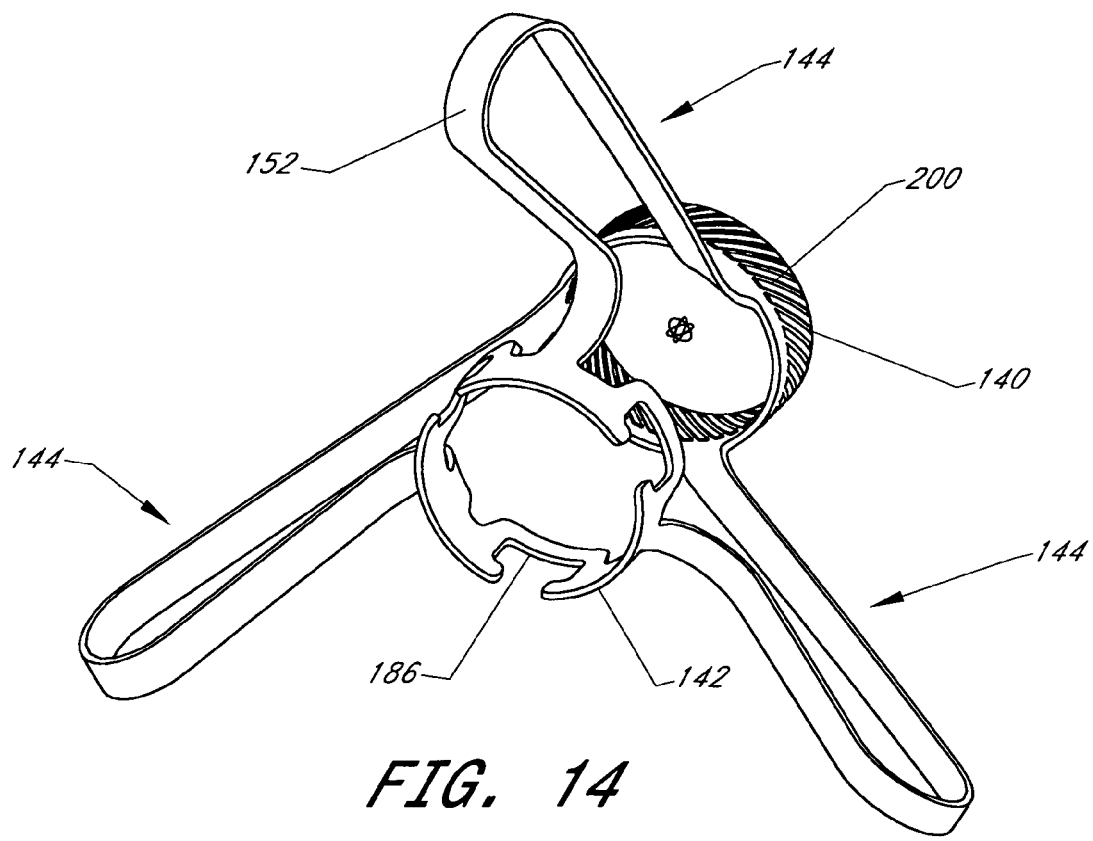
FIG. 14 is a perspective view of an alternative embodiment of the proximal anchor.
Figure 18:
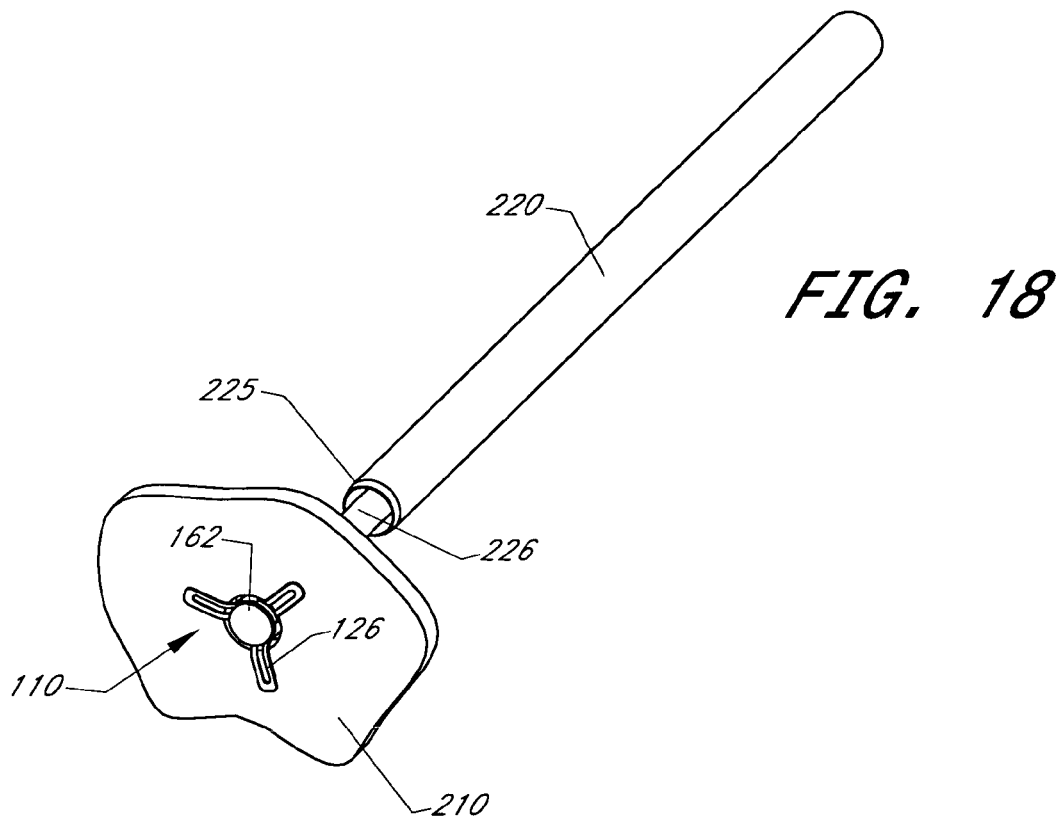
FIG. 18 is a perspective view of the distal anchor and sensor of FIG. 17 with the delivery catheter further retracted.

FIGS. 13 and 14 illustrate the proximal and distal anchors of FIGS. 10-12 with the addition of a plurality of radiopaque markers 200 for facilitating visualization of the assembly under fluoroscopy during deployment. As shown, radiopaque markers 200 can be applied to the legs 124 of the distal anchor 110 and/or to the proximal ring 140 of the proximal anchor 112. Radiopaque markers can also be provided on other portions of the proximal anchor 112, the distal anchor 110 and/or the sensor 120. The radiopaque markers are preferably placed in "low flex zones," such as the tips of the distal anchor legs 124 and the proximal ring 140 of the proximal anchor. Generally, "low flex zones" are portions of the anchor that experience substantially minimal flexing or bending. This insures that the materials used in the radiopaque markers do not negatively affect the elasticity of the flexing anchor sections, and also insures that the radiopaque materials to not separate from the anchor within a patient.

Radiopaque markers are typically made of noble metals, such as gold, platinum/iridium, tantalum, etc, and are typically attached to the anchor by selective plating or ion beam deposition. Alternatively, the markers could be micro rivets and/or rings that are mechanically attached to portions of the system components. In order to reduce the risk of galvanic corrosion which can be experienced by dissimilar metals exposed to blood, the radiopaque material can be selected to have a galvanic corrosion potential that is substantially similar to a galvanic corrosion potential of the material from which the anchors and/or sensor are made. For example, if the anchors 110, 112 are to be made of NITINOL, the radiopaque markers 200 can be made of tantalum. Alternatively, an electrically insulating coating (conformal coatings) such as parylene or other biocompatible synthetic material can be used to cover the radiopaque markers in order to isolate the marker and anchor section from exposure to the blood or other bodily fluid.

FIGS. 15-21 illustrate embodiments of systems and methods for delivering and deploying the anchor assembly 100 to secure a sensor 120 in a septum wall 210. According to one embodiment, a guidewire is placed through the septum wall 210 at the target site. A dilator sheath can then be fed over the guide wire and into the left atrium. The guidewire and dilator sheath can then be removed. A delivery catheter can then be fed over the dilator sheath until it crosses the septum and enters the left atrium.

As shown in FIGS. 15 and 16, an assembly 100 of a proximal anchor 112, a distal anchor 110 and a sensor 120 is provided within an introducer sheath configured to introduce the anchor assembly into the proximal end of the delivery catheter 220. A stylet 224 is advanced through a central lumen of the electrical lead 226 to provide column strength and guidance to the device.

The introducer sheath containing the anchor and sensor assembly is then inserted into the proximal end of the delivery catheter, and the sheath is retracted and withdrawn. The anchor assembly is then guided through the delivery catheter 220 (which was previously positioned through the septum wall) until the legs of the distal anchor 110 are positioned at the distal end of the delivery catheter 220, which can be visually verified under fluoroscopy by noting the position of the distal radiopaque marker 225 on the distal edge of the delivery catheter 220. The delivery catheter 220 can be withdrawn while holding the anchor and sensor assembly 100 in place with the stylet 224 extending through the center of the sensor lead 226. The stylet 224 is preferably configured to provide sufficient column strength to allow the anchor and sensor assembly 100 to be held in place relative to the septum 210 while the catheter 220 is retracted to expose and deploy the anchors.

Figure 19:
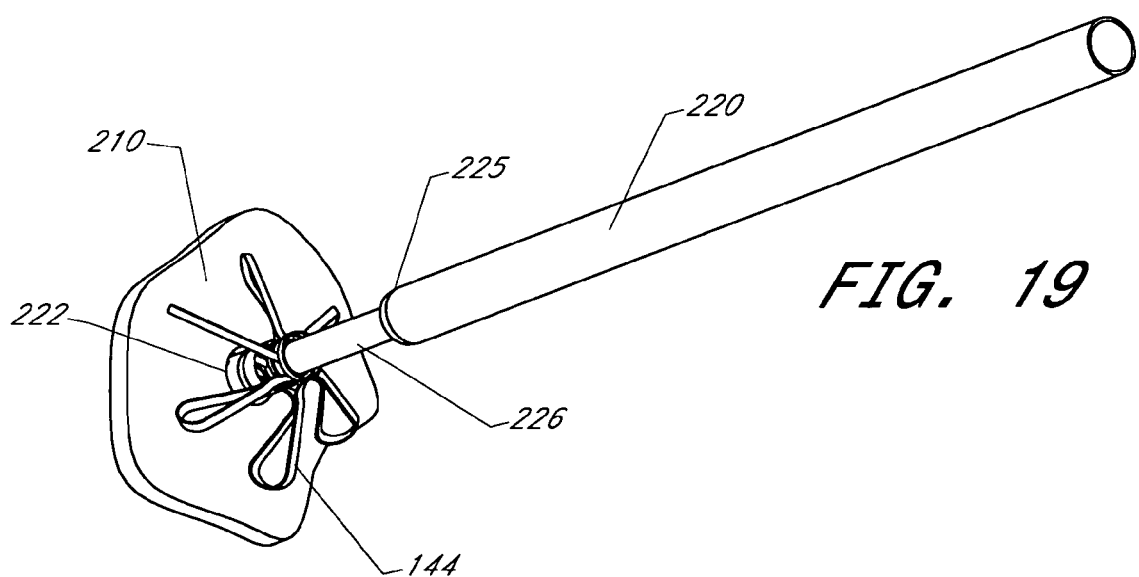
FIG. 19 is a perspective view illustrating a delivery catheter deploying an anchor and sensor assembly as viewed from a proximal side of an atrial septum wall.

As the catheter 220 is retracted to expose the distal anchor 110, the distal anchor legs 124 will expand to assume their expanded state on a distal side of the septum wall 210. Continued retraction of the catheter 220 will expose the proximal anchor 112, allowing it to relax to its expanded state on a proximal side of the septum wall 210 as shown in FIG. 19. The fully deployed proximal 112 and distal 110 anchors preferably resiliently engage the septum wall 210 in order to firmly secure the sensor 120 to the septum wall 210.

Figure 20:
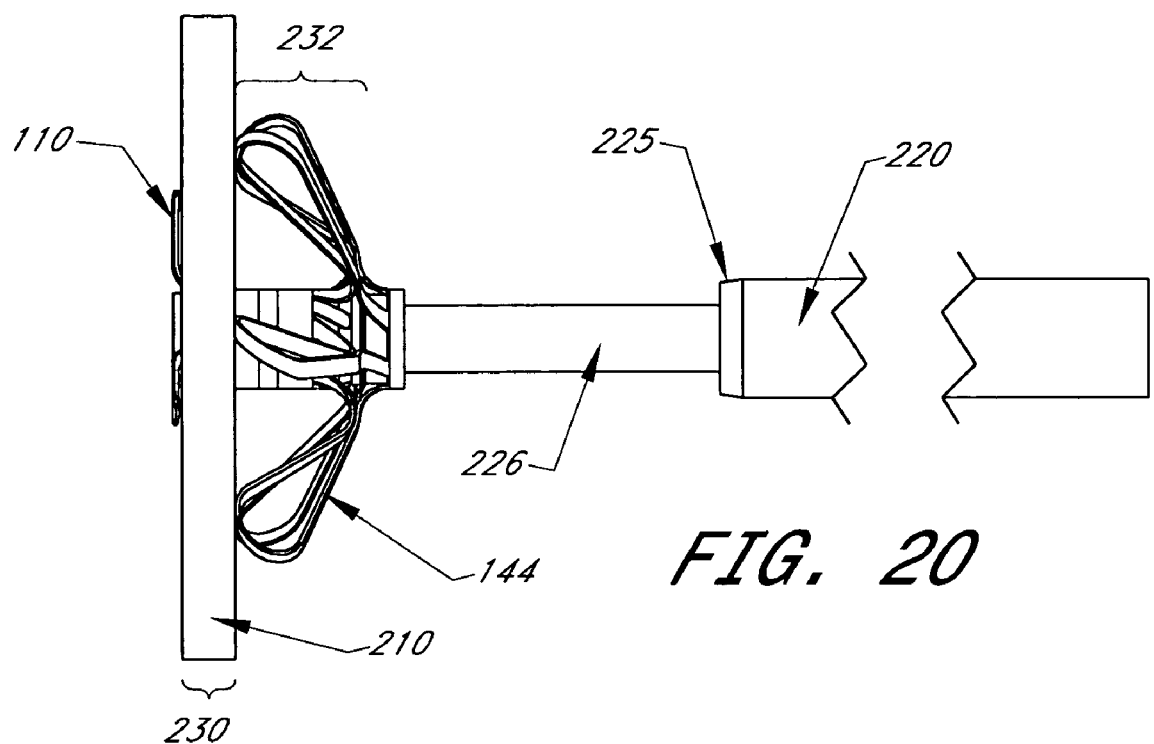
FIG. 20 is a side view of an anchor and sensor assembly deployed and anchored to a thin atrial septum wall (shown in cross-section).
Figure 21:
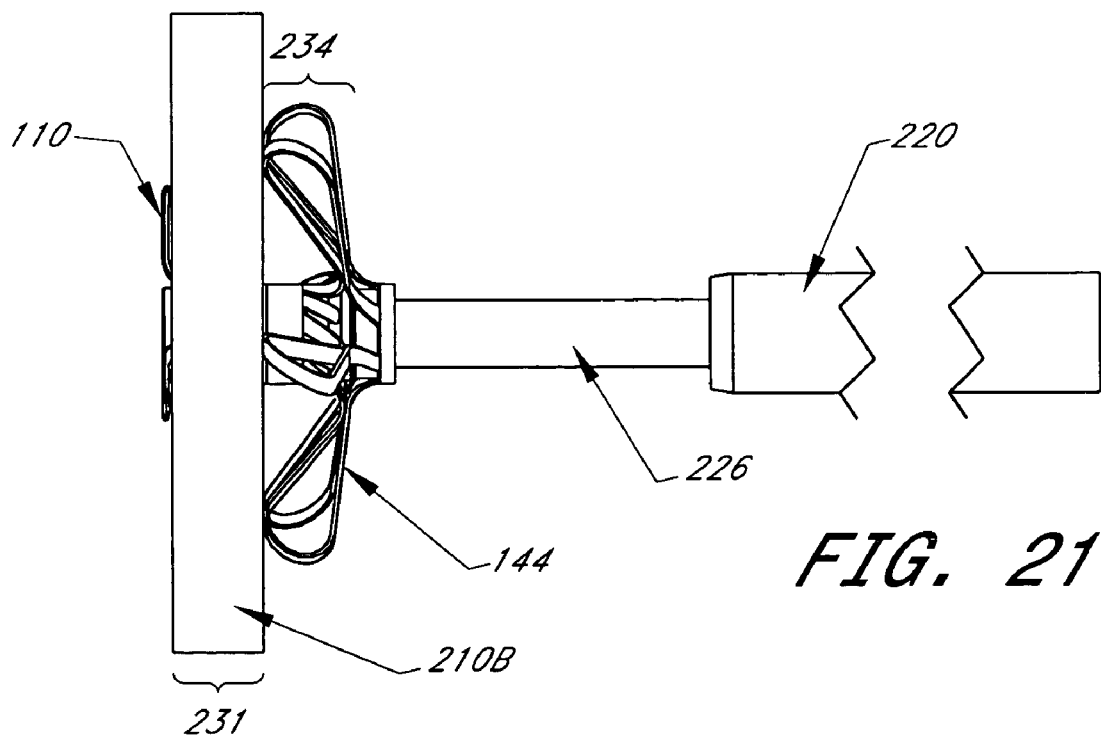
FIG. 21 is a side view of an anchor and sensor assembly deployed and anchored to a thicker atrial septum wall (shown in cross-section).
Figure 22:
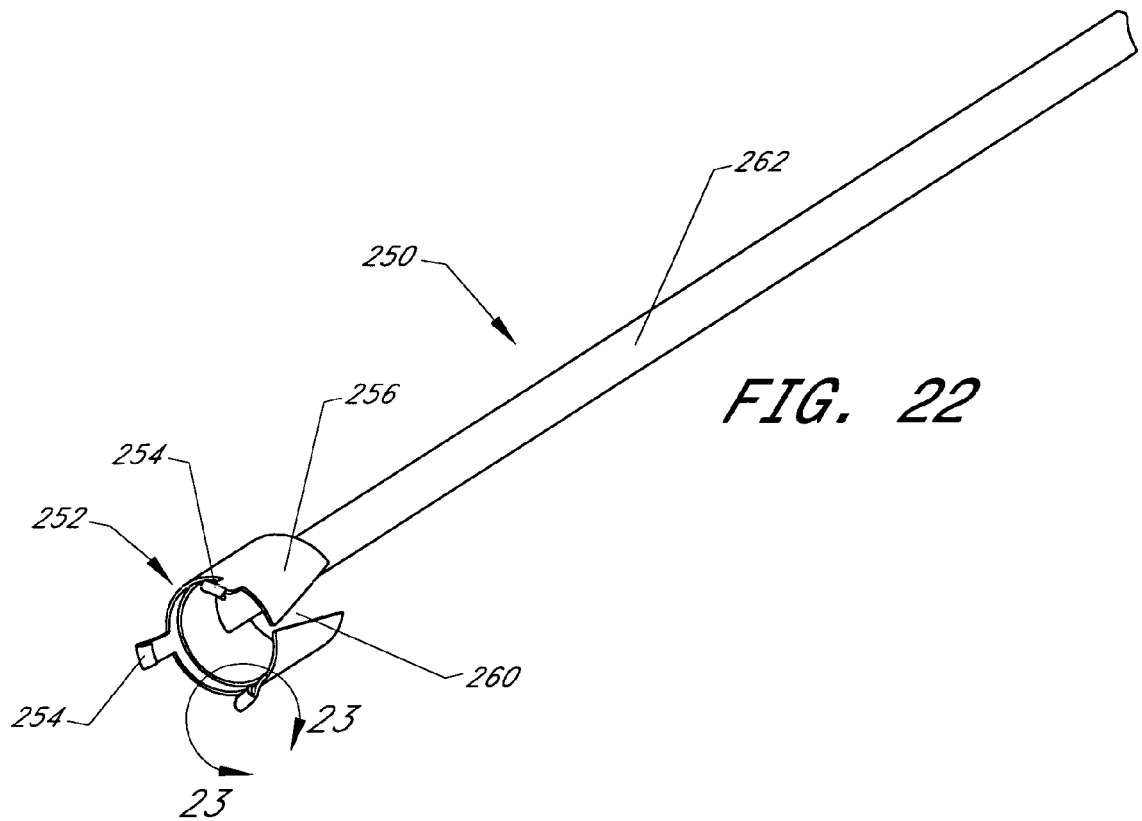
FIG. 22 is a perspective view of one embodiment of a retrieval device for retrieving the anchor and sensor assembly.

In one embodiment, the legs 144 of the proximal anchor 112 apply a lower spring force to the septum wall 210 than the legs 124 of the distal anchor 110 so that variations in septum wall thickness are accommodated by variations in the position of the proximal anchor legs 144 as shown in FIGS. 20 and 21. FIG. 20 shows a relatively thin septum wall 210 with a thickness 230. In order to securely anchor the sensor, the legs 144 of the proximal anchor 112 will extend distally until their distal motion is stopped by the pressure of the septum wall 210. In the embodiment of FIG. 21, the septum wall 210 is substantially thicker 231, thereby causing the legs 144 of the proximal anchor 112 to extend a shorter distance distally than in the embodiment of FIG. 20. This difference in anchored position of the proximal anchor legs 144 can also be seen in the difference in the dimensions 232 and 234. As shown in FIGS. 20 and 21, the distance 232 in FIG. 20 between the proximal edge of the proximal ring 140 and the proximal surface of the septum wall 210 is greater than a corresponding distance 234 for the thicker septum wall 210B of FIG. 21.

In one embodiment, the lead 226 shown in FIGS. 16, 19 and 20 is part of a pressure monitoring apparatus and is used to relay electrical signals to a signaling device as described, for example, in the Eigler patent mentioned above.

FIGS. 22-35 illustrate systems and methods for retrieving an anchor and sensor assembly 100 from its position anchored to a septum wall 210. Retrieval devices having preferred features and advantages are generally configured to be placed within a catheter and guided to the location of the anchor and sensor assembly 100 within a patient. A retrieval device can then be operated to grasp the anchor assembly 100 and draw it into a lumen of the catheter for removal from the patient's body.

In one embodiment, a retrieval apparatus 250 such as that shown in FIGS. 22-27 generally comprises a retrieval head 252 with a plurality of grasping hooks 254 extending distally from a cylindrical body 256. The cylindrical body 256 of the retrieval head 252 comprises as small an axial length as possible in order to allow the retrieval device to be easily guided through the tortuous anatomy of a patient's vasculature.

Figure 23:
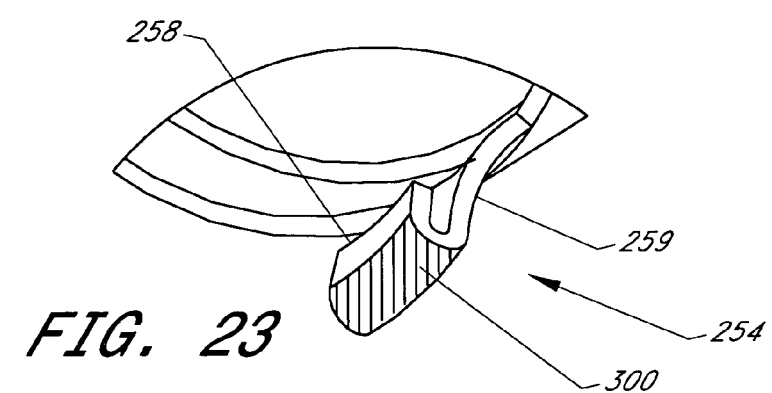
FIG. 23 is a detail view of a portion of the retrieval device of FIG. 22, taken through line 23-23.
Figure 24:
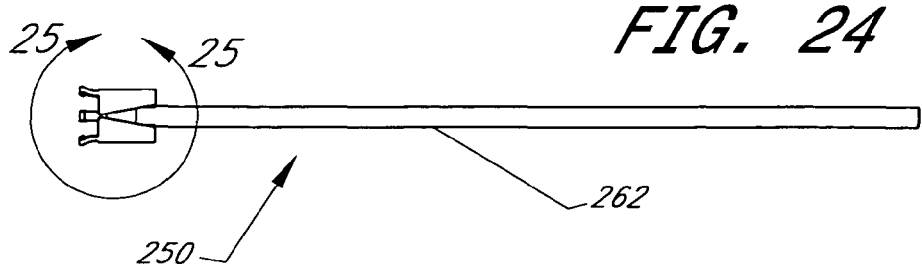
FIG. 24 is a side view of one embodiment of a retrieval device.
Figure 25:
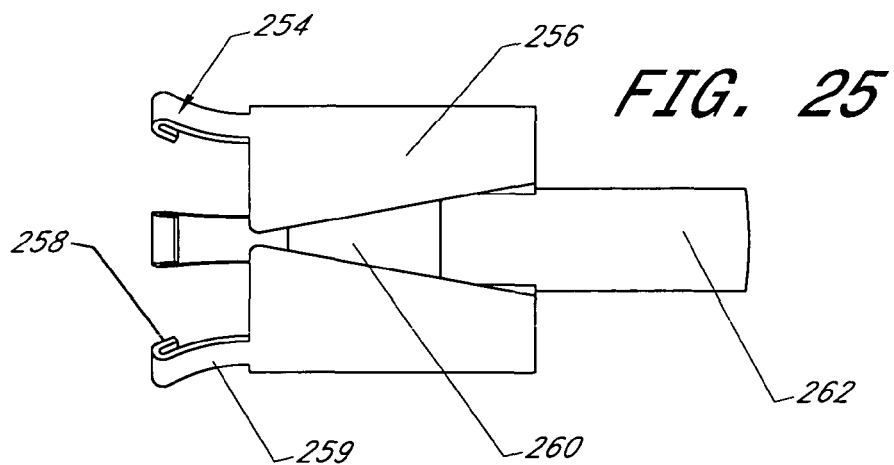
FIG. 25 is a detail view of the retrieval head of the retrieval device of FIG. 24.
Figure 26:
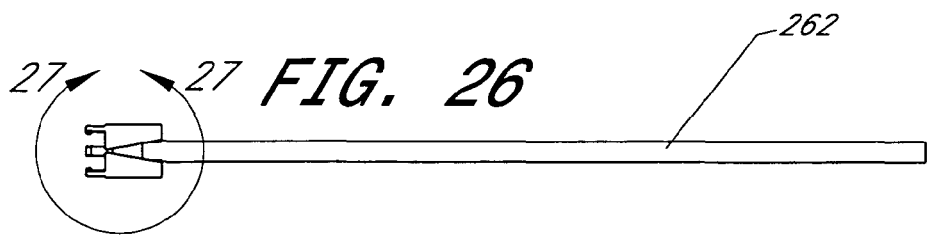
FIG. 26 is a side view of one embodiment of a retrieval device.
Figure 27:
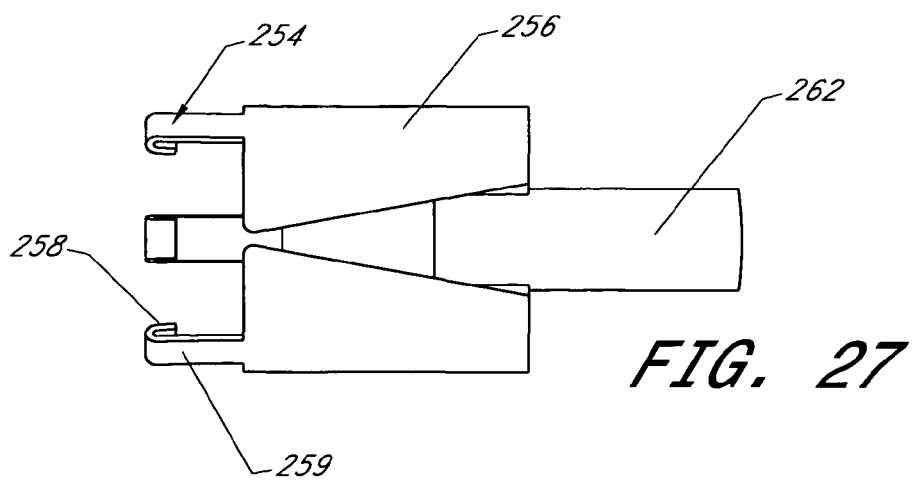
FIG. 27 is a detail view of the retrieval head of the retrieval device of FIG. 26.
Figure 31:
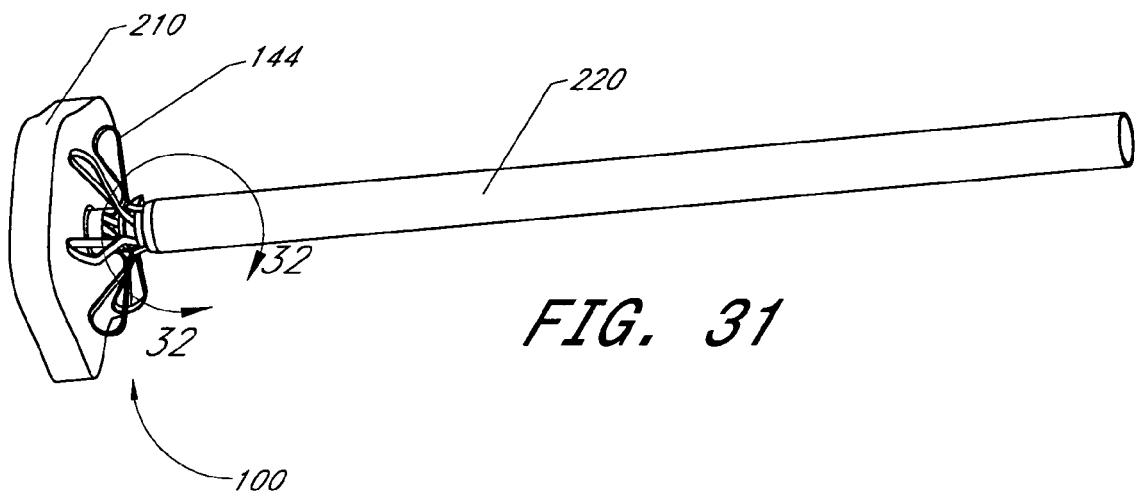
FIG. 31 is a side perspective view illustrating a retrieval device positioned for retrieving the anchor and sensor assembly.
Figure 32:
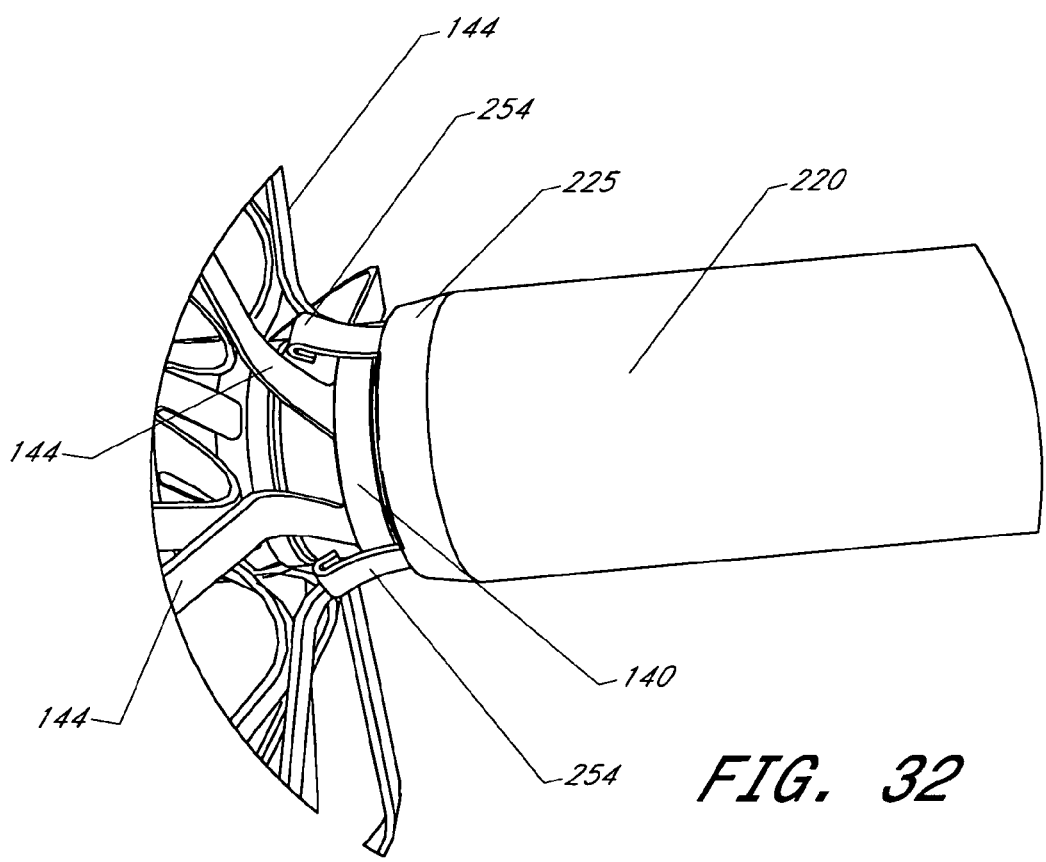
FIG. 32 is a detail view of the retrieval device and the anchor and sensor assembly of FIG. 31 taken through line 32-32.
Figure 33:
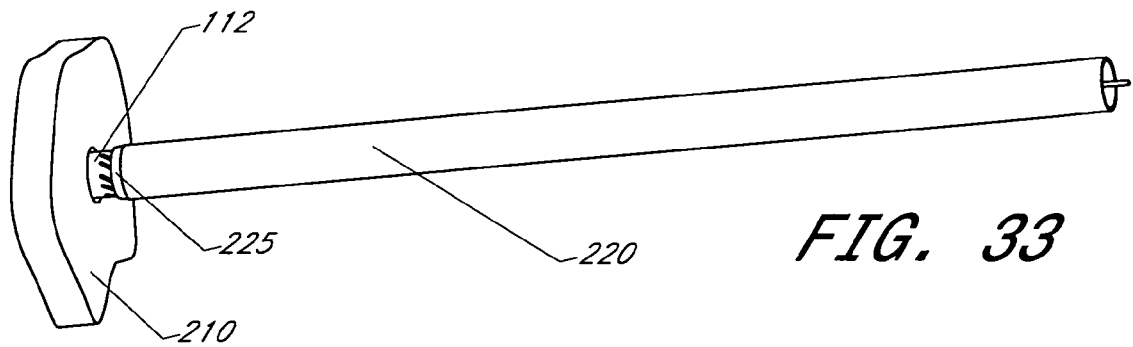
FIG. 33 is a side perspective view of the retrieval device and the anchor and sensor assembly of FIG. 31, shown with the proximal anchor partially withdrawn into the retrieval catheter.
Figure 34:
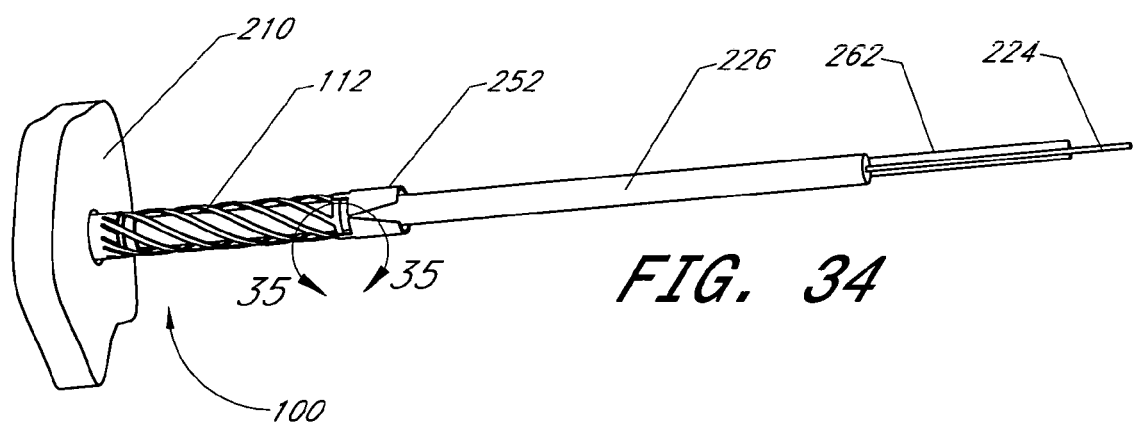
FIG. 34 is the side perspective view of FIG. 33 shown with the catheter removed to show detail.
Figure 35:
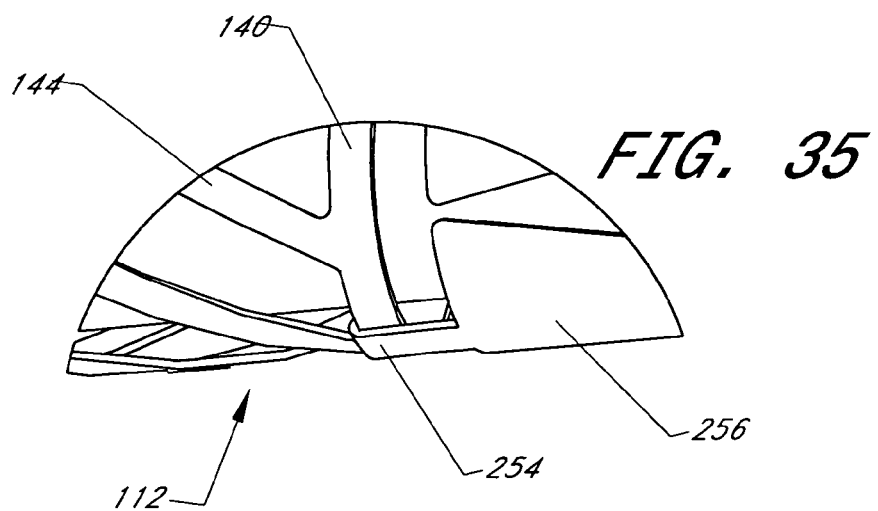
FIG. 35 is a detail view of a portion of the retrieval device of FIG. 34, taken through line 35-35.

With reference to FIG. 23, the grasping hooks 254 can be configured to comprise return legs 258 which are substantially parallel to the attachment portion of the legs 259. In their relaxed position, the legs 259 are bent radially outwards as shown in FIGS. 24 and 25 in order to allow the hooks 254 to be advanced distally past the proximal ring 140. When the retrieval device 250 is drawn into the catheter, the legs 254 assume a compressed state as shown in FIGS. 26 and 27. In their compressed state, the legs 259 are substantially parallel to the longitudinal axis of the cylindrical body 256 of the retrieval device 250.

As shown in FIGS. 22-27, the cylindrical body 256 can include a slot 260 configured to allow the retrieval head to allow the retrieval device 250 to be assembled onto the lead by "side loading," e.g, by placing the cylindrical body 256 beside the lead and pressing the lead 226 sideways through the slot 260 of the cylindrical body 256. This is particularly advantageous in embodiments in which the lead 226 comprises an enlarged proximal end (such as an electrical connector), since side-loading the retrieval head onto the lead 226 allows the retrieval head to have an internal diameter only slightly larger than the diameter of the lead.

In an alternative embodiment, the retrieval head 252 can be configured to be moved from an open position to a closed position by compressing the cylindrical body 256 to a smaller diameter. According to this embodiment, the slot 260 in the cylindrical body 256 is provided to allow the retrieval head to expand to assume an internal diameter that is sufficiently large that the cylindrical body 256 can be fed over a sensor lead 226 (e.g. see FIG. 34). The retrieval head of this embodiment can be constricted to assume a smaller diameter, and to cause the grasping hooks to engage the proximal anchor.

FIGS. 28-30 illustrate an alternative embodiment of a retrieval device 280 that comprises a retrieval head 252 with a plurality of helical legs 282 extending between and attached to proximal 284 and distal 286 rings. The construction of the retrieval device 280 advantageously allows the device to be more easily guided through a patient's tortuous vasculature. The proximal ring 284 of the retrieval device 280 can be configured to receive an attachment loop 278 of a push/pull ribbon 262. The retrieval device 280 also includes a plurality of grasping hooks 292 for engaging and removing the anchor and sensor assembly 100. This embodiment is also advantageously longer than the previous retriever embodiment in order to allow it to be extended further out of the delivery catheter. With reference to the detail view of FIG. 29, the grasping hooks 292 generally include attachment legs 294 and return legs 296. The return legs 296 as shown, are oriented to be substantially perpendicular to a longitudinal axis of the retrieval device 282. The return legs 296 also preferably include radiopaque markers 300 to facilitate visualization of the distal end of the retrieval device 280 under fluoroscopy.

The retrieval devices 250, 280 are generally configured such that the grasping hooks 254, 292 can be moved between an "open" or expanded position and a "closed" position. In the open position, the hooks 254, 292 are spaced sufficiently to be placed distally of the proximal ring 140 of the proximal anchor 112 The grasping hooks 254, 292 can be moved to their closed position for example by advancing the catheter 220 distally relative to the retrieval device 250, 280. The distal edge of the catheter 220 will compress the hooks 254, 292 to their-closed position. In the alternative embodiment of FIGS. 26 and 27, the device can be moved to a closed position by radially compressing the cylindrical body 256 of the retrieval device. In order to fully engage the hooks on the proximal ring, the ribbon 262 can be pulled proximally slightly.

Methods of retrieving the anchor and sensor assembly will now be described with reference to FIGS. 31-35. Once a retrieval device 250, 280 is in position with the grasping hooks 254, 292 engaged on a proximal ring 140 of the proximal anchor 112, the retrieval device 250, 280 is pulled proximally until the proximal ring 140 of the proximal anchor 112 enters the distal end of the delivery catheter 220. At this point, the radiopaque markers of the retrieval device (300), the proximal ring 140 and the delivery catheter (220) are all aligned with one another. The stylet 224 is then held fixed to maintain the position of the sensor while the proximal anchor 112 is stretched, causing it to compress, by drawing back both the catheter and the retrieval implant. Once the proximal anchor 112 is stretched to its compressed state, it can be introduced into the catheter 220 by holding the ribbon 262 stationary and advancing the delivery catheter 220 over the proximal anchor 112, while holding the sensor 120, the proximal anchor 112 and distal anchor 110 substantially stationary with the stylet 224.

Once the proximal anchor 112 has been is fully compressed and is contained within the catheter 220, the catheter 220 can be advanced distally while holding the retrieval device stationary. The catheter is advanced until the distal edge of the catheter extends through the septum wall 210 and is positioned adjacent the legs 124 of the distal anchor 110. The legs 124 of the distal anchor 110 can be compressed by further advancing the catheter 220 distally while pulling the ribbon 262 proximally, and allowing the stylet to move proximally. Once the legs 124 of the distal anchor 110 have been fully compressed, the distal anchor can be pulled back into the lumen of the catheter 220. The catheter 220 containing the anchors 110, 112 and the sensor 120 can then be removed from the patient's vasculature.

Additionally, removal of a chronically implanted device can also involve the adjunctive use of a commercial cardiac lead removal system including a lead grasping stylet, such as a SPECTRANETICS LEAD LOCKING DEVICE (LLD™ model 518-018, 518-019, or 518-021) and/or a suitable lead removal sheath or excimer laser lead removal catheter, such as a SPECTRANETICS LASER SHEATH (SLSII™ model 500-001, 500-012, or 500-013). The skilled artisan will recognize that additional equipment can also be used in order to effectively remove an implanted anchor device from within a patient.

In most situations, it is not necessary to remove the sensor from an implant site, however in some situations removal may be necessary. In general, the reasons for removing the anchor and sensor assembly from its position anchored to a septum wall might include: incorrect placement of the device, device failure, infections, etc. As mentioned above, the hole through which the sensor and anchor assembly 100 extends is preferably formed by stretching a very small guidewire access hole. Thus, upon removal of the sensor and anchor assembly from the septum wall, the hole will typically substantially collapse to a small size. In time, the hole will typically heal on its own. If necessary, however any one of a number of devices and systems for closing septal defects can be used to substantially close a hole in the septum wall.

In some embodiments, it is desirable to provide one or more radiopaque markers on one or more of the system components in order to facilitate visualization of the various system components under fluoroscopy during deployment or retrieval procedures and/or to verify correct placement of the anchor and sensor assembly 100 after deployment. Radiopaque markers can advantageously allow a physician to visually confirm a location of the device within a patient during placement and retrieval of the sensor assembly 100. As shown throughout the Figures, in several embodiments, radiopaque markers can be applied to portions of one or more of the proximal and distal anchors 110 and 112 (e.g. see markers 200 in FIGS. 10-14), the delivery and/or retrieval catheters 220 (e.g. see markers 225 in FIGS. 15-21, 32 and 33), the retrieval heads 252 (e.g. see markers 300 in FIGS. 23 and 29), and the sensor itself. In some embodiments, the sensor can comprise components made of a sufficiently dense material, including but not limited to zirconia ceramic materials, such that portions of the sensor itself are radiopaque.

Radiopaque markers can be formed on the various system components by any suitable process or method. For example, in some embodiments, the markers are plated or ion deposited onto portions of the system components. The radiopaque markers are preferably placed in "low flex zones" of the system components such as the tips of the distal anchor legs 124, the proximal ring 140 of the proximal anchor 112, and the return legs 258, 296 of the grasping hooks 254, 292. Generally, "low flex zones" are portions of a device that experience substantially minimal flexing or bending. This insures that the materials used in the radiopaque markers do not negatively affect the elasticity of the flexing sections, (e.g. the flexing anchor legs) and also insures that the radiopaque materials to not undesirably delaminate from the devices within a patient due to differences in ultimate strain values of the materials of the anchor and the markers.

Radiopaque markers are typically made of noble metals, such as gold, platinum/iridium, tantalum, etc. In order to reduce the risk of galvanic corrosion which can be experienced by dissimilar metals exposed to blood, the radiopaque material can be selected to have a galvanic corrosion potential that is substantially similar to a galvanic corrosion potential of the material from which the anchors, retrieval device(s) and/or the sensor are made. For example, if the anchors 110, 112 are to be made of NITINOL, the radiopaque markers 200 can be made of tantalum to reduce the possibility of galvanic corrosion. Alternatively, an electrically insulating or conformal coatings such as parylene or other biocompatible synthetic material can be used to cover the radiopaque markers in order to isolate the marker and/or other metallic sections from exposure to the blood.

The apparatus and methods of the present invention may be embodied in other specific forms and for other applications without departing from its spirit or essential characteristics. The described embodiments are to be considered in all respects only as illustrative and not restrictive.

Although certain embodiments and examples have been described herein, it will be understood by those skilled in the art that many aspects of the methods and devices shown and described in the present disclosure may be differently combined and/or modified to form still further embodiments. Additionally, it will be recognized that the methods described herein may be practiced using any device suitable for performing the recited steps. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined only by a fair reading of the claims that follow.

Additionally, the skilled artisan will recognize that the embodiments of anchoring devices and methods described herein may be advantageously applied for anchoring any other diagnostic and/or therapeutic implant to a wall of any organ within a patient. In addition to sensors, such implants include, but are not limited to, sensing and stimulating electrodes, ultrasound transducers, drug delivery systems, pacing leads, electrocardiogram leads, oxygen partial pressure sensors, oxygen saturation sensors, or any other device that one desires to securely anchor to a wall of an internal organ. It will also be apparent to one skilled in the art that the field of use of the embodiments of devices and methods described herein extends beyond the specific condition of heart failure to any cardiovascular condition or other condition in a medical patient where a device is implanted through a wall of a chamber or vessel is affixed to a wall of that chamber of vessel.

What is claimed is:

1. A retrieval device configured to retrieve a cardiac anchoring device from a position deployed in a wall of an organ within a patient, the retrieval device comprising:
    a retrieval head comprising a proximal end region, a distal end, and a plurality of grasping hooks extending from the distal end;
    a ribbon attached to the proximal end region of the retrieval head, wherein the ribbon is configured to extend from a retrieval location within a patient to a location outside of the patient; and
    wherein the grasping hooks are configured to engage a proximal ring of a proximal anchor, wherein the retrieval head further comprises a distal ring near the distal end, a proximal retrieval head ring, and a plurality of helical legs extending between the proximal retrieval head ring and the distal ring, and wherein the grasping hooks extend distally from the distal ring.

2. The retrieval device of claim 1, wherein the grasping hooks comprise return legs oriented so as to be substantially perpendicular to a longitudinal axis of the retrieval device.

3. The retrieval device of claim 1, wherein the grasping hooks comprise return legs oriented so as to be substantially parallel to a longitudinal axis of the retrieval device.

4. The retrieval device of claim 1, wherein the retrieval head comprises a substantially cylindrical body with an axial slot extending along a wall of the substantially cylindrical body, the axial slot configured to permit the diameter of the cylindrical body to increase or decrease.

5. The retrieval device of claim 4, wherein the axial slot extends along the entire length of the substantially cylindrical body's wall, thereby allowing the retrieval head to be assembled onto a lead by side loading.

6. The retrieval device of claim 1, wherein the retrieval head comprises an internal diameter configured to allow the retrieval head to pass over a sensor lead.

7. The retrieval device of claim 1, wherein the helical legs pass through a substantially whole number of complete circles between the proximal retrieval head ring and the distal ring.

8. The retrieval device of claim 1, wherein each grasping hook comprises a radiopaque marker.

* * * * *

UNITED STATES PATENT AND TRADEMARK OFFICE
CERTIFICATE OF CORRECTION

| | | |
|---|---|---|
| PATENT NO. | : 7,890,186 B2 | Page 1 of 1 |
| APPLICATION NO. | : 11/633819 | |
| DATED | : February 15, 2011 | |
| INVENTOR(S) | : Wardle et al. | |

It is certified that error appears in the above-identified patent and that said Letters Patent is hereby corrected as shown below:

In column 9 at line 29, change "serise" to --sense--.

In column 13 at line 13, change "112 The" to --112. The--.

In column 13 at line 17, change "their-closed" to --their closed--.

Signed and Sealed this
Twenty-fifth Day of October, 2011

David J. Kappos
*Director of the United States Patent and Trademark Office*